US012590959B2

(12) United States Patent
Chan et al.

(10) Patent No.: US 12,590,959 B2
(45) Date of Patent: Mar. 31, 2026

(54) SYSTEMS AND METHODS FOR MEASURING CELL SIGNALING PROTEIN ACTIVITY

(71) Applicant: Octant, Inc., Emeryville, CA (US)

(72) Inventors: Henry Chan, Emeryville, CA (US); Aaron Cooper, Berkeley, CA (US); Molly Jeanette Gasperini, Oakland, CA (US)

(73) Assignee: Octant, Inc., Emeryville, CA (US)

( * ) Notice: Subject to any disclaimer, the term of this patent is extended or adjusted under 35 U.S.C. 154(b) by 993 days.

(21) Appl. No.: 17/590,712

(22) Filed: Feb. 1, 2022

(65) Prior Publication Data

US 2022/0244253 A1 Aug. 4, 2022

Related U.S. Application Data

(60) Provisional application No. 63/144,766, filed on Feb. 2, 2021.

(51) Int. Cl.
| | |
|---|---|
| *C07K 14/47* | (2006.01) |
| *C07K 14/72* | (2006.01) |
| *C12Q 1/527* | (2006.01) |
| *C12Q 1/6897* | (2018.01) |
| *G01N 33/50* | (2006.01) |
| *G01N 33/566* | (2006.01) |

(52) U.S. Cl.
CPC ......... *G01N 33/566* (2013.01); *C07K 14/723* (2013.01); *C12Q 1/527* (2013.01); *C12Q 1/6897* (2013.01); *G01N 33/5041* (2013.01); *G01N 2333/4719* (2013.01); *G01N 2333/726* (2013.01)

(58) Field of Classification Search
None
See application file for complete search history.

(56) References Cited

U.S. PATENT DOCUMENTS

| | | | |
|---|---|---|---|
| 5,750,341 | A | 5/1998 | Macevicz |
| 5,969,119 | A | 10/1999 | Macevicz |
| 6,306,597 | B1 | 10/2001 | Macevicz |
| 7,170,050 | B2 | 1/2007 | Turner et al. |
| 7,211,390 | B2 | 5/2007 | Rothberg et al. |
| 7,244,559 | B2 | 7/2007 | Rothberg et al. |
| 7,244,567 | B2 | 7/2007 | Chen et al. |
| 7,264,929 | B2 | 9/2007 | Rothberg et al. |
| 7,276,720 | B2 | 10/2007 | Ulmer |
| 7,302,146 | B2 | 11/2007 | Turner et al. |
| 7,313,308 | B2 | 12/2007 | Turner et al. |
| 7,315,019 | B2 | 1/2008 | Turner et al. |
| 7,323,305 | B2 | 1/2008 | Leamon et al. |
| 7,335,762 | B2 | 2/2008 | Rothberg et al. |
| 7,405,281 | B2 | 7/2008 | Xu et al. |
| 7,462,452 | B2 | 12/2008 | Williams et al. |
| 7,462,468 | B1 | 12/2008 | Williams et al. |
| 7,476,503 | B2 | 1/2009 | Turner et al. |
| 7,476,504 | B2 | 1/2009 | Turner |
| 7,491,498 | B2 | 2/2009 | Lapidus et al. |
| 7,501,245 | B2 | 3/2009 | Quake et al. |
| 2002/0142436 | A1 | 10/2002 | Antoni et al. |
| 2006/0024678 | A1 | 2/2006 | Buzby |
| 2006/0024711 | A1 | 2/2006 | Lapidus et al. |
| 2006/0286566 | A1 | 12/2006 | Lapidus et al. |
| 2008/0087826 | A1 | 4/2008 | Harris et al. |
| 2008/0103058 | A1 | 5/2008 | Siddiqi |
| 2008/0206764 | A1 | 8/2008 | Williams et al. |
| 2008/0213770 | A1 | 9/2008 | Williams et al. |
| 2009/0024331 | A1 | 1/2009 | Tomaney et al. |
| 2009/0029385 | A1 | 1/2009 | Christians et al. |
| 2009/0061439 | A1 | 3/2009 | Buzby |
| 2009/0068655 | A1 | 3/2009 | Williams |
| 2012/0077706 | A1 | 3/2012 | Lee et al. |

FOREIGN PATENT DOCUMENTS

| | | |
|---|---|---|
| WO | WO-2009045463 A1 | 4/2009 |
| WO | WO-2020243164 A1 | 12/2020 |

OTHER PUBLICATIONS

Velasquez et al. (2018) Molec. Pharmacol. 94: 963-972. (Year: 2018).*

Altschul, S. et al, "Basic Local Alignment Search Tool", J. Mol. Biol, 1990, vol. 215, pp. 403-410.

Chinn, AM, et al., Involvement of the cyclic AMP pathway in dendritic cell regulation of Th2 immune responses. The FASEB Journal. Apr. 2016;30:969-19, abstract only.

Inda, C, et al., "Different CAMP sources are critically involved in G protein-coupled receptor CRHR1 signaling", Journal of Cell Biology, Jul. 18, 2016, vol. 214, No. 2, pp. 181-195.

International Search Report and Written Opinion dated Apr. 6, 2022 for International Application No. PCT/US2022/014758.

Johnstone, TB, et al., "PDE8 is Expressed in Human Airway Smooth Muscle and Selectively Regulates cAMP Signaling by β2-Adrenergic Receptors and Adenylyl Cyclase 6", American Journal of Respiratory Cell and Molecular Biology, Apr. 2018, vol. 58, No. 4, pp. 530-541.

Karlin, S. et al., "Methods for assessing the statistical significance of molecular sequence features by using general scoring schemes", PNAS, 1990, vol. 87, pp. 2264-2268.

Karlin, S. et al., "Applications and statistics for multiple high-scoring segments in molecular sequences", PNAS, 1993, vol. 90, pp. 5873-5877.

Lin, W.W., et al., "Roles of atypical protein kinase C in lysophosphatidic acid-induced type II adenylyl cyclase activation in RAW 264.7 macrophages", British Journal of Pharmacology, Nov. 1999, vol. 128, No. 6, pp. 1189-1198.

Strazzabosco, M, et al., Differentially Expressed Adenylyl Cyclase Isoforms Mediate Secretory Functions in Cholangiocyte Subpopulation, Hepatology, Jul. 2009, vol. 50, No. 1, pp. 244-252.

(Continued)

*Primary Examiner* — Michael D Pak

(74) *Attorney, Agent, or Firm* — Wilson Sonsini Goodrich & Rosati

(57) ABSTRACT

Described herein are systems for measuring enzymatic activities. Also described herein are methods for measuring or screening enzymatic activities utilizing the systems described herein.

18 Claims, 5 Drawing Sheets

Specification includes a Sequence Listing.

(56)  References Cited

OTHER PUBLICATIONS

Margulies, M. et al., Genome sequencing in microfabricated high-density picolitre reactors, Nature, 2005, vol. 437, pp. 376-380.

Deans et al.: A Tunable Genetic Switch Based on RNAi and Repressor Proteins for Regulating Gene Expression in Mammalian Cells. Cell. Elseveier. 130(2):363-372 (2007).

EP22750254.9 European Search Report dated Dec. 4, 2024.

Wieland et al.: Engineering Molecular Circuits Using Synthetic Biology in Mammalian Cells. Annual Review of Chemical and Biomolecular Engineering. 3(1):209-234 (2012).

Japanese Patent Application No. 2023-546435 Office Action dated Jan. 14, 2026.

Kolodecik et al.: Molecule Page. Soluble Adenylyl Cyclase. The Pancreapedia. 1-6 (2011).

Wettschureck et al.: Mammalian G Proteins and Their Cell Type Specific Functions. Physiol Rev. 85(4):1159-1204 (2005).

Yang et al.: G protein-coupled receptors: structure- and function-based drug discovery. Signal Transduction and Targeted Therapy. 6(7):1-27 (2021).

* cited by examiner

Fig. 2A

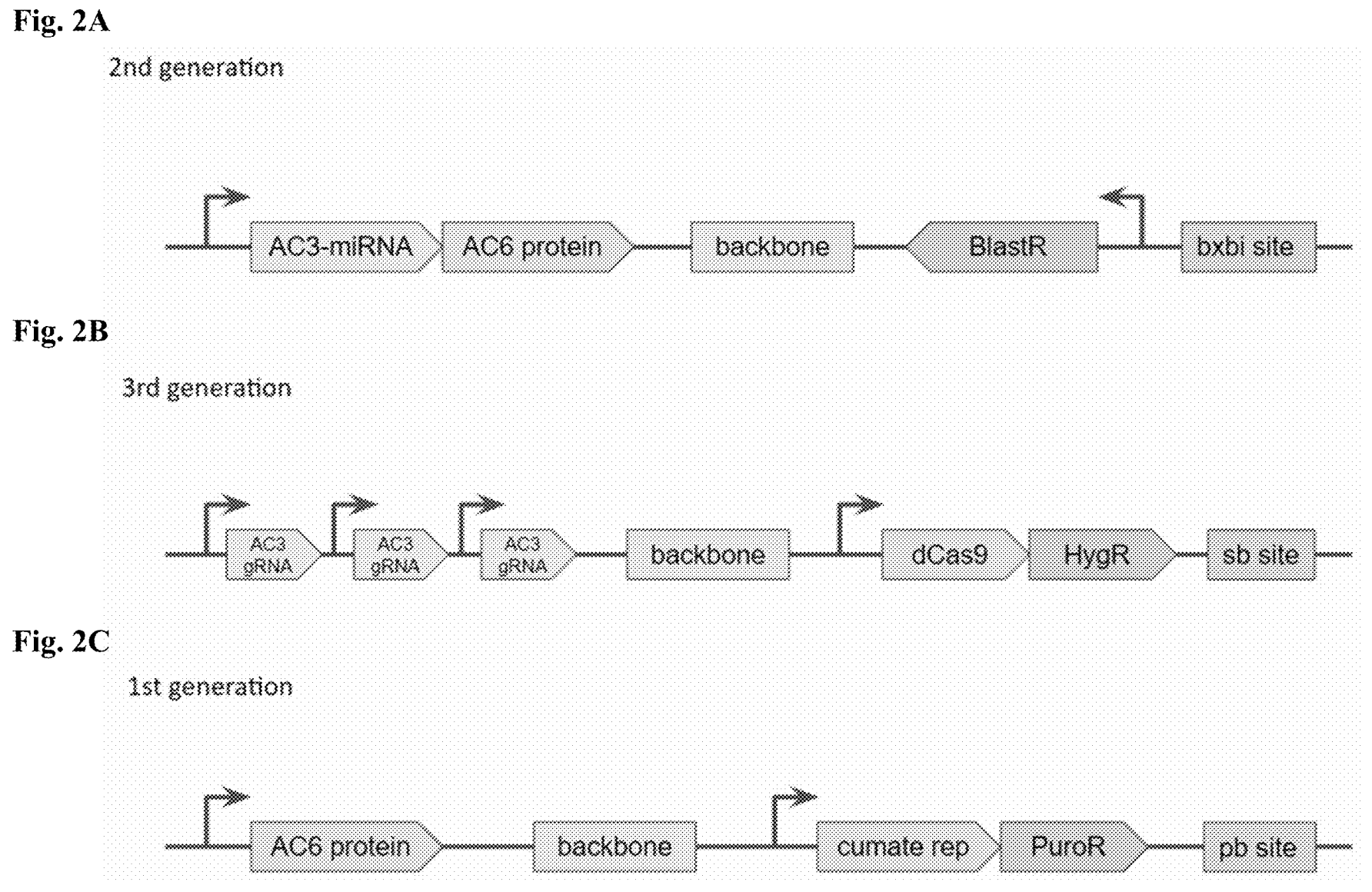

2nd generation

AC3-mRNA | AC6 protein | backbone | BlastR | bxbi site

Fig. 2B

3rd generation

AC3 gRNA | AC3 gRNA | AC3 gRNA | backbone | dCas9 | HygR | sb site

Fig. 2C

1st generation

AC6 protein | backbone | cumate rep | PuroR | pb site

SEQUENCE LISTING

<160> NUMBER OF SEQ ID NOS: 4

<210> SEQ ID NO 1
<211> LENGTH: 11087
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aatctaacgt taataaaata tctttatttt cattacatct gtgtgttggt tttttgtgtg      60
aatcgatagt actaacatac gctctccatc aaaacaaaac gaaacaaaac aaactagcaa     120
aataggctgt ccccagtgca agtgcaggtg ccagaacatt tctcttaaga gactagttat     180
taatagtaat caattacggg gtcattagtt catagcccat atatggagtt ccgcgttaca     240
taacttacgg taaatggccc gcctggctga ccgcccaacg acccccgccc attgacgtca     300
ataatgacgt atgttcccat agtaacgcca atagggactt tccattgacg tcaatgggtg     360
gagtatttac ggtaaactgc ccacttggca gtacatcaag tgtatcatat gccaagtccg     420 cccctattg acgtcaatga cggtaaatgg cccgcctggc attatgccca gtacatgacc     480
ttacgggact ttcctacttg gcagtacatc tacgtattag tcatcgctat taccatggtg     540
atgcggtttt ggcagtacac caatgggcgt ggatagcggt ttgactcacg gggatttcca     600
agtctccacc ccattgacgt caatgggagt ttgttttggc accaaaatca acgggacttt     660
ccaaaatgtc gtaataccc cgccccgttg acgcaaatgg gcaagcttgc cgggtcgagg     720
taggcgtgta cggtgggagg cctatataag caaccggtat aatcaaacag accagattgt     780
ctgtttgtta ccggtgttta gtgaaccggg cgtttagtga ctcctgcagg ccctaagtga     840
ccagctacag tcggaaacca tcagcaagca ggtatgtact ctccagggtg gggaatctcc     900
cgccctgctc gctcagctga tctgtggctt gcgacgagca gcatgagcgt gattgagttt     960
tgaacgctca tgctgctcgt cgtattagtt acatcagtcg gttttcgtcg agggccccaa    1020

-continued

```
cccacctcct acgatcaacg atccaagaag gtatattgct gttgacagtg agcgatacgt   1080
cgtactgcca gcgctttagt gaagccacag atgtagcgct ggcagtacga cgtgtttgcc   1140
tactgcctcg gacttcaagg gagatgtctc aacggcagct tagctacagt ctttcttcat   1200
gtgactcgtg gactacgcgc gaagttcagg cccagagaat atatgaaggg gcctgaactt   1260
cgcgcgtgtt gttcaattgt catcactggc atcttttttg agctccctgg cttccccagt   1320
caagactcca gggatttgag ggacgctgtg gcctcttctc ttacatgtac cttttgctag   1380
cctcaaccct gactatcttc caggtcattg ttccaacatg cacttgacag ccaccatgtc   1440
atggtttagt ggactcctgg tccctaaagt ggatgaacgg aaaacagcct ggggtgaacg   1500
aaatggacag aagcgttcga gaaggcgtgg cactagggct ggtggattct gcacgcctcg   1560
ctatatgagc tgcctcagag atgcagagcc acccagccca accctgctg gaccacctag    1620 atgcccttgg caggatgacg ccttcatcag aagggggagga ccaggaaagg gaaaggagtt   1680
gggtctgaga gcagtggctc tgggtttcga ggataccgag gtgacaacga cagcaggagg   1740
aacggctgag gtggcacctg acgcagtgcc caggagtggg cgatcctgct ggaggcgtct   1800
ggtgcaggta ttccagtcga agcagttccg ttcggccaag ctggagcgcc tgtaccagcg   1860
gtacttcttc cagatgaacc agagcagcct gacgctgctg atggcggtgc tggtgctgct   1920
cacagcggtg ctgctggctt tccacgctgc tcctgctcgc cctcagcctg cttatgtggc   1980
actgttggcc tgtgcagcag cactgttcgt gggactcatg gtggtgtgta acagacattc   2040
tttcagacag gactccatgt gggtggtgag ctacgtggtg ctgggcatcc tggcagcagt   2100
gcaggtcgga ggagcactcg cagcagaccc tcgcagcccc tctgcgggac tctggtgccc   2160
tgtgttcttt gtctacatcg cctacacgct cctccccatc cgcatgagag ctgccgtcct   2220
cagcggactg ggactctcca ccttgcattt gatcttggcc tggcaactta accgtggtga   2280
tgccttcctc tggaagcagc tcggtgccaa tgtgctgctg ttcctctgca ccaacgtcat   2340
tggcatctgc acacactatc cagcagaggt gtctcagcgc caggcctttc aggaaacccg   2400
cggttacatc caggcccggc tccatctgca gcatgagaat cggcagcagg agcggctgct   2460
gctgtcggta ttgccccagc acgttgcaat ggagatgaaa gaagatatta acacaaaaaa   2520
agaggacatg atgttccaca aaatctacat acagaagcat gacaatgtca gcatcctgtt   2580
tgcagacatt gagggcttca ccagcctggc atcccagtgc actgcgcagg agctggtcat   2640
gaccctgaat gagctgtttg cccggtttga caagctggct gcggagaatc actgcctgag   2700
gatcaagatt ttggggggact gttactactg tgtgtcaggg ctgccggagg cacgggccga   2760
ccatgcccac tgctgtgtgg agatgggggt agacatgatt gaggccatct cgctggttcg   2820
tgaggtgaca ggagtgaatg tgaacatgcg cgtgggcatc cacagcgggc gcgtgcactg   2880
cggcgtcctt ggcttgcgga aatggcagtt cgatgtgtgg tccaatgatg tgaccctggc   2940
caaccacatg gaggcaggag gccgggctgg ccgcatccac atcactcggg caacactgca   3000
gtacctgaac ggggactacg aggtggagcc aggccgtggt ggcgagcgca atgcgtacct   3060
caaggagcag cacattgaga ctttcctcat cctgggcgcc agccagaaac ggaaagagga   3120
gaaggccatg ctggccaagc tgcagcggac tcgggccaac tctatggaag ggctgatgcc   3180
gcgctgggtt cctgatcgtg ccttctcccg gaccaaggac tccaaggcct ccgccagat    3240 gggcattgat gattccagca aagacaaccg gggcacccaa gatgccctga ccctgaggga   3300
tgaggtggat gagttcctga gccgtgccat cgacgcccgc agcattgatc agctgcggaa   3360
ggaccatgtg cgccggtttc tgctcacctt ccagagagag gatcttgaga agaagtactc   3420
```

```
ccggaaggtc gatccccgct tcggagccta cgttgcctgt gccctgttgg tcttttgctt    3480
catctgcttc atccagcttc tcatcttccc acactccacc ctgatgcttg ggatctatgc    3540
cagcatcttc ctgctgctgc taatcaccgt gctgatctgt gctgtgtact cctgtggttc    3600
tctgttccct aaggccctgc aacgtctgtc ccgcagcatt gtccgctcac gggcacatag    3660
caccgcagtt ggcatctttt ccgtcctgct tgtgtttact tctgccattg ccaacatgtt    3720
cacctgtaac cacaccccca tacggagctg tgcagcccgg atgctgaatt taacaccagc    3780
tgacatcact gcctgccatc tgcagcagct caattactct ctgggcctgg atgctcccct    3840
gtgtgagggc accatgccta cctgcagctt tcctgagtat ttcatcggga acatgctgct    3900
gagtctcttg gccagctctg ttttcctgca catcagcagc atcgggaagt tggccatgat    3960
ctttgtcttg gggctcatct atttggtgct gcttctgctg ggtcccccag ccaccatctt    4020
tgacaactat gacctactgc ttggcgttca tggcttggct tcttccaatg aaacctttga    4080
tgggctggac tgtccagctg cagggagggg ggccctcaaa tatatgaccc ctgtgattct    4140
gctggtgttt gcgctggcgc tgtatctgca tgctcagcaa gtggagagca ctgcccgcct    4200
agacttcctc tggaaaactac aggcaacagg ggagaaggag gagatggagg agctacaggc    4260
atacaaccgg aggctgctgc ataacattct gcccaaggac gtggcggccc acttcctggc    4320
tcgggagcgc cgcaatgatg aactctacta tcagtcgtgc gagtgtgtgg ctgttatgtt    4380
tgcctccatt gccaacttct ctgagttcta tgtggagctg gaggcaaaca atgagggtgt    4440
cgagtgcctg cggctgctca acgagatcat cgctgacttt gatgagatta tcagcgagga    4500
gcggttccgg cagctggaaa agatcaagac gattggtagc acctacatgg ctgcctcagg    4560
gctgaacgcc agcacctacg atcaggttgg ccgctcccac atcactgccc tggctgacta    4620
cgccatgcgg ctcatggagc agatgaagca catcaatgag cactccttca acaatttcca    4680
gatgaagatt gggctgaaca tgggcccagt cgtggcagga gtcatcgggg ctcggaagcc    4740
acagtatgac atctggggga acacagtgaa tgtctctagt cgtatggaca gcacgggggt    4800
ccccgaccga atccaggtta ccacggacct gtaccaggtt ctagctgcca agggctacca    4860
gctggagtgt cgaggggtgg tcaaggtgaa gggcaagggg gagatgacca cctacttcct    4920
caatgggggc cccagcagtt aactcgagcc cctctccctc ccccccccct aacgttactg    4980
gccgaagccg cttggaataa ggccggtgtg cgtttgtcta tatgttattt tccaccatat    5040
tgccgtcttt tggcaatgtg agggcccgga aacctggccc tgtcttcttg acgagcattc    5100
ctaggggtct ttcccctctc gccaaaggaa tgcaaggtct gttgaatgtc gtgaaggaag    5160
cagttcctct ggaagcttct tgaagacaaa caacgtctgt agcgaccctt gcaggcagc    5220 ggaacccccc acctggcgac aggtgcctct gcggccaaaa gccacgtgta taagatacac    5280
ctgcaaaggc ggcacaaccc cagtgccacg ttgtgagttg atagttgtg gaaagagtca    5340 aatggctctc ctcaagcgta ttcaacaagg gctgaagga tgcccagaag gtaccccatt    5400
gtatgggatc tgatctgggg cctcggtgca catgctttac atgtgtttag tcgaggttaa    5460
aaaacgtcta ggccccccga accacgggga cgtggttttc ctttgaaaaa cacgatgata    5520
atatggccac aaccatgaaa acgatcatcg ccctgagcta catcttctgc ctggtattcg    5580
ccgactacaa ggacgatgat gacgccagca tcgatggatc catggcagga gcaccaggac    5640
ccctgcgctt ggctttgctc ttgcttggga tggttgggcg ggctgggcct cgaccccaag    5700
gcgcaaccgt ttcactgtgg gaaactgttc aaaagtggcg agaatatcgg cgccaatgcc    5760
```

-continued

```
aacggtcttt gactgaggac ccacctccag ccaccgatct gttctgtaac cgcaccttcg    5820
acgaatatgc ctgttggcca gacggggaac cagggtcctt cgtcaatgtc tcctgtcctt    5880
ggtatctgcc ctgggcatcg tctgtccctc aagggcatgt ctaccgattc tgcacagccg    5940
aaggcctgtg gctccaaaag gacaactcct ccttgccttg gcgggacctg tctgagtgtg    6000
aggagtctaa acgaggagag cggtcatctc cggaggaaca actgcttttc ttgtatatca    6060
tatataccgt cggctacgca ctgtctttct ccgcacttgt catcgcttcc gccattctcc    6120
tgggatttcg ccacctgcac tgcacgcgaa attacattca tctgaatctg tttgcgtctt    6180
ttatactccg cgcactgtct gtctttatca aagacgctgc gttaaagtgg atgtattcca    6240
ctgccgcgca acaacatcaa tgggatgggc tgctgtccta tcaagattca ctgtcctgtc    6300
gcctggtttt ccttcttatg caatattgtg ttgccgcaaa ctactattgg ctgctggttg    6360
aaggcgttta cctgtatact ctgctcgctt tttctgttct ctccgaacaa tggatattcc    6420
gactttatgt ctctattggc tggggcgttc ccctgctgtt cgttgtcccg tgggggatcg    6480
ttaagtacct atatgaggat gagggatgtt ggacacgaaa ttccaacatg aattactggc    6540
ttatcattcg gctccctatt ctcttcgcta tcggcgtcaa ctttctcatt ttcgttcgcg    6600
tcatttgcat agtcgtttca aaactcaaag ctaatttaat gtgcaagacc gatattaagt    6660
gtcggttagc taagtctaca cttacactaa taccactttt gggaacacac gaggttattt    6720
ttgctttcgt catggatgaa cacgcccgcg gcaccttgcg ctttataaag ttgttcactg    6780
agttatcctt tacctctttt caaggcctca tggtcgccat tttgtattgt ttcgtcaata    6840
acgaagtcca acttgaattt cggaagtcat gggaacgctg gcggctagag cacttgcaca    6900
tacaacgaga ttcatccatg aaacctctca agtgcccaac ctcatcatta tcatctggcg    6960
ccaccgccgg ctcctccatg tatactgcca catgtcaagc ctcatgctcc taatagcgaa    7020
ttccctgtga cccctcccca gtgcctctcc tggccttgga agttgccact ccagtgccca    7080
ccagccttgt cctaataaaa ttaagttgca tcattttgtc tgactaggtg tcctctataa    7140
tattatgggg tggaggggggg tggtatggag caaggggccc aagttgggaa gacaacctgt    7200
agggcctgcg gggtctattc gggaaccaag ctggagtgca gtggcacaat cttggctcac    7260
tgcaatctcc gcctcctggg ttcaagcgat tctcctgcct cagcctcccg agttgttggg    7320
attccaggca tgcatgacca ggctcagcta attttttgttt ttttggtagt gacggggttt    7380
caccatattg gccaggctgg tctccaactc ctaatctcag gtgatctacc caccttggcc    7440
tcccaaattg ctgggattac aggcgtgaac cactgctccc ttccctgtcc ttcctaggtc    7500
gtccacgatc agctagaatc aagctagata aactggccgt cgttttacac gggtgggcct    7560
ttcttcggta gaaaatcaaa ggatcttctt gagatccttt ttttctgcgc gtaatctgct    7620
gcttgcaaac aaaaaaacca ccgctaccag cggtggtttg tttgccggat caagagctac    7680
caactctttt ccgaggtaa ctggcttcag cagagcgcag ataccaaata ctgttcttct    7740
agtgtagccg tagttaggcc accacttcaa gaactctgta gcaccgccta catacctcgc    7800
tctgctaatc ctgttaccag tggctgctgc cagtggcgat aagtcgtgtc ttaccgggtt    7860
ggactcaaga cgatagttac cggataaggc gcagcggtcg gctgaacggg ggggttcgtg    7920
cacacagccc agcttggagc gaacgaccta caccgaactg agatacctac agcgtgagct    7980
atgagaaagc gccacgcttc ccgaagggag aaaggcggac aggtatccgg taagcggcag    8040
ggtcggaaca ggagagcgca cgagggagct tccagggggga aacgcctggt atctttatag    8100
tcctgtcggg tttcgccacc tctgacttga gcaccgattt ttgtgatgct cgtcaggggg    8160
```

-continued

```
gcggagccta tggaaaaacg ccagcaacgc agaaaggccc acccgaaggt gagccaggtg   8220
attacattta ggtcctcatt agaaaaactc atcgagcatc aagtgaaact gcaatttatt   8280
catatcagga ttatcaatac catatttttg aaaaagccgt ttctgtaatg aaggagaaaa   8340
ctcaccgagg cagttccata ggatggcaag atcctggtat cggtctgcga ttccgactcg   8400
tccaacatca atacaaccta tcagtttccc ctcgtcaaaa ataaggttat caagtgagaa   8460
atcaccatga gtgacgactg aatccggtga gaatggcaag agtttatgca tttctttcca   8520
gacttgttca acaggccagc cattacgctc gtcatcaaaa tcactcgcac caaccaaacc   8580
gttattcatt cgtgattgcg cctgagccag acgaaatacg cgatcaccgt taaaaggaca   8640
attacaaaca ggaatcgaat gcaaccggcg caggaacact gccagcgcat caacaatatt   8700
ttcacctgaa tcaggatatt cttctaatac ctggaatgct gttttccctg ggatcgcagt   8760
ggtgagtaac catgcatcat caggagtacg gataaaatgc ttgatggtcg gaagaggcat   8820
aaattccgtc agccagttta gcctgaccat ctcatctgta acatcattgg caacgctacc   8880
tttgccatgt ttcagaaaca actctggcgc atcgggcttc ccatacaatc ggtagattgt   8940
cgcacctgat tgcccgacat tatcacgagc ccatttatac ccatataaat cagcatccat   9000
gttggaattt aatcgcggct tcaagcaaga cgtttcccgt tgaatatggc tcattttagc   9060
ttccttagct cctgaaaatc tcgataactc aaaaaatacg cccggtagtg atcttatttc   9120
attatggtga agttggaac ctcttacgtg ccgatcaagt caaaagcctc cggtcggagg   9180
cttttgactt tctgctatgg aggtcaggta tgatttaaat ggtcagtatt gagcctcagg   9240
aaacagctat gaccatgatc gctgactaga taatctagcg tcgtgacgca cgcgtgccat   9300
agagcccacc gcatccccag catgcctgct attgtcttcc caatcctccc ccttgctgtc   9360
ctgccccacc ccacccccca gaatagaatg acacctactc agacaatgcg atgcaatttc   9420
ctcattttat taggaaagga cagtgggagt ggcaccttcc agggtcaagg aaggcacggg   9480
ggaggggcaa acaacagatg ctggcaact agaaggcaca gtcgggccgc gatgattttc   9540
atatgccctt gagcacagaa attaagcaga ggctaattat gtgatatgat ttaaggttgg   9600
gtctatatag ttatagcttg atgagttaaa ttggattagg agtttgcaag atgatttggc   9660
acagttagtc atagacgaag gacttacttt gaaccagcgg tttcagttgt caatcttgga   9720
tttcagcgac agcccgcagc ccttcaaatt aattaacgag attagttcct ggtgtacttg   9780 aggggatga gttcctcaat ggtggttttg accagcttgc cattcatctc aatgagcaca   9840
aagcagtcag gagcatagtc agagatcagc tctctacaca tgccacaggg gctgaccacc   9900
ctgatggatc tgtccacctc atcagagtag gggtgcctga cagccacaat ggtgtcaaag   9960
tccttctgcc cgttgctcac agcagaccca atggcaatgg cttcagcaca gacagtgacc   10020
ctgccaatgt aggcttcaat gtggacagca gagatgatct ccccagtctt ggtcctgatg   10080
gccgccccga catggtgctt gttgtcctca tagagcatgg tgatcttctc agtggcgacc   10140
tccaccagct ccagatcctg ctgagagatg ttgaaggttt tcatagggcc gggattctcc   10200
tccacgtcac cgcatgttag aagacttcct ctgccctcgc gagatccggt ggagccgggt   10260
ccggcggtgc cgtccacggc agaattggac gactgagcgc gggatctggc gaaggcgatg   10320
ggggtcttga aggcgtgctg gtactccacg atgcccagct cggtgttgct gtgcagctcc   10380
tccacgcggg ggaaggcgaa catggggccc ccgttctgca ggatgctggg gtggatggca   10440
ctcttgaagt gcatgtggct gtccaccacg aagctgtagt agccgccgtc gcgcaggctg   10500
```

-continued

```
aaggtgcggg cgaagctgcc caccagcacg ttatcgccca tggggtgcag gtgctccacg    10560
gtggcgttgc tgcggatgat cttgtcggtg aagatcacgc tgtcctcggg gaagccggtg    10620
cccaccacct tgaagtcgcc gatcacgcgg ccggcctcgt agcggtagct gaagctcacg    10680
tgcagcacgc cgccgtcctc gtacttctcg atgcgggtgt tggtgtagcc gccgttgttg    10740
atggcgtgca ggaaggggtt ctcgtagccg ctggggtagg tgccgaagtg gtagaagccg    10800
tagcccatca cgtggctcag caggtagggg ctgaaggtca gggcgccttt ggtgctcttc    10860
atcttgttgg tcatgcggcc ctgcttgggg gtgccctctc cgccgcccac cagctcgaac    10920
tccacgccgt tcagggtgcc ggtgatgcgg cactcgatct ccatggcggg caggccgctc    10980
tcgtcgctct ccatggtggc ggcggtcgcc cttattacta ccccggatga tcctgacgac    11040
ggagaccgcc gtcgtcgaca agccggaagc ttgtgcactc tcagtac                    11087
```

```
<210> SEQ ID NO 2
<211> LENGTH: 11134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

```
gagggcctat ttcccatgat tccttcatat ttgcatatac gatacaaggc tgttagagag      60
ataattagaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaaggagc cgagccagcc gagtccgttt aagagctatg ctggaaacag catagcaagt     300
ttaaataagg ctagtccgtt atcaacttga aaaagtggca ccgagtcggt gcttttttga     360
acgctgacgt catcaacccg ctccaaggaa tcgcgggccc agtgtcacta ggcgggaaca     420
cccagcgcgc gtgcgccctg gcaggaagat ggctgtgagg gacaggggag tggcgccctg     480
caatatttgc atgtcgctat gtgttctggg aaatcaccat aaacgtgaaa tgtctttgga     540
tttgggaatc ttataagttc tgtatgagac cactctttcc cagtgcacag ctattccccg     600
cggtttaaga gctatgctgg aaacagcata gcaagtttaa ataaggctag tccgttatca     660
acttgaaaaa gtggcaccga gtcggtgctt ttttctaga gatccgacgc cgccatctct      720
aggcccgcgc cggccccctc gcacagactt gtgggagaag ctcggctact cccctgcccc     780
ggttaatttg catataatat ttcctagtaa ctatagaggc ttaatgtgcg ataaaagaca     840
gataatctgt tctttttaat actagctaca ttttacatga taggcttgga tttctataag     900
agatacaaat actaaattat tattttaaaa aacagcacaa aaggaaactc accctaactg     960
taaagtaatt gtgtgttttg agactataaa tatgcatgcg agaaaagcct tgtttgggcc    1020
ctggggctga ggctcaggtt taagagctat gctggaaaca gcatagcaag tttaaataag    1080
gctagtccgt tatcaacttg aaaaagtggc accgagtcgg tgcttttttc gaatttaaat    1140
cggatccgcg gccgcaatca acctctggat tacaaaattt gtgaaagatt gactggtatt    1200
cttaactatg ttgctccttt tacgctatgt ggatacgctg ctttaatgcc tttgtatcat    1260
gcgttaacta aacttgttta ttgcagctta taatggttac aaataaagca atagcatcac    1320
aaatttcaca ataaagcat ttttttcact gcattctagt tgtggtttgt ccaaactcat    1380
caatgtatct tatcatgtct gtaagaggtt ccaactttca ccataatgaa ataagatcac    1440
```

```
taccgggcgt attttttgag ttatcgagat tttcaggagc taaggaagct aaaatgagta   1500
ttcaacattt ccgtgtcgcc cttattccct tttttgcggc attttgcctt cctgtttttg   1560
ctcacccaga aacgctggtg aaagtaaaag atgctgaaga tcagttgggt gcacgagtgg   1620
gttacatcga actggatctc aacagcggta agatccttga gagtttacgc cccgaagaac   1680
gttttccaat gatgagcact tttaaagttc tgctatgtgg cgcggtatta tcccgtattg   1740
acgccgggca agagcaactc ggtcgccgca tacactattc tcagaatgac ttggttgaat   1800
actcaccagt cacagaaaag catctcacgg atggcatgac agtaagagaa ttatgcagtg   1860
ctgccataac catgagtgat aacactgcgg ccaacttact tctggcaacc atcggaggac   1920
cgaaggagct aaccgctttt ttgcacaaca tgggggatca tgtaactcgc cttgatcgtt   1980
gggaaccgga gctgaatgaa gccataccaa acgacgagcg tgacaccacg atgcctgtag   2040
caatggcaac aacgttgcgc aaactattaa ctggcgaact acttactcta gcttcccggc   2100
aacaactgat agactggatg gaggcggata aagttgcagg atcacttctg cgctcggccc   2160
tcccggctgg ctggtttatt gctgataaat ctggagccgg tgagcgtggc tctcgcggta   2220
tcattgcagc actggggcca gatggtaagc cctcccgcat cgtagttatc tacacgacgg   2280
ggagtcaggc aactatggat gaacgaaata gacagatcgc tgagataggt gcctcactga   2340
ttaagcattg gtaatgaggg ccctgaggac ctaaatgtaa tcacctggct caccttcggg   2400
tgggcctttc tgcgttgctg gcgtttttcc ataggctccg cccccctgac gagcatcaca   2460
aaaatcggtg ctcaagtcag aggtggcgaa acccgacagg actataaaga taccaggcgt   2520 ttcccctgg aagctccctc gtgcgctctc ctgttccgac cctgccgctt accggatacc   2580
tgtccgcctt tctcccttcg ggaagcgtgg cgctttctca tagctcacgc tgtaggtatc   2640
tcagttcggt gtaggtcgtt cgctccaagc tgggctgtgt gcacgaaccc cccgttcagc   2700
ccgaccgctg cgccttatcc ggtaactatc gtcttgagtc caacccggta agacacgact   2760
tatcgccact ggcagcagcc actggtaaca ggattagcag agcgaggtat gtaggcggtg   2820
ctacagagtt cttgaagtgg tggcctaact acggctacac tagaagaaca gtatttggta   2880
tctgcgctct gctgaagcca gttacctcgg aaaaagagtt ggtagctctt gatccggcaa   2940
acaaaccacc gctggtagcg gtggtttttt tgtttgcaag cagcagatta cgcgcagaaa   3000
aaaaggatct caagaagatc ctttgataag gatctgcgat cgctccggtg cccgtcagtg   3060
ggcagagcgc acatcgccca cagtccccga gaagttgggg ggaggggtcg gcaattgaac   3120
gggtgcctag agaaggtggc gcggggtaaa ctgggaaagt gatgtcgtgt actggctccg   3180
cctttttccc gagggtgggg gagaaccgta tataagtgca gtagtcgccg tgaacgttct   3240
ttttcgcaac gggtttgccg ccagaacaca gctgaagctt cgaggggctc gcatctctcc   3300
ttcacgcgcc cgccgcccta cctgaggccg ccatccacgc cggttgagtc gcgttctgcc   3360
gcctcccgcc tgtggtgcct cctgaactgc gtccgccgtc taggtaagtt taaagctcag   3420
gtcgtgaccg ggcctttgtc cggcgctccc ttggagccta cctagactca gccggctctc   3480
cacgctttgc ctgaccctgc ttgctcaact ctacgtcttt gtttcgtttt ctgttctgcg   3540
ccgttacaga tccaagctgt gaccggcgcc tacgctagac gccaccatgg acaagaagta   3600
cagcatcggc ctggccatcg gcaccaactc tgtgggctgg gccgtgatca ccgacgagta   3660
caaggtgccc agcaagaaat tcaaggtgct gggcaacacc gaccggcaca gcatcaagaa   3720
gaacctgatc ggcgccctgc tgttcgacag cggagaaaca gccgaggcca cccggctgaa   3780
gagaaccgcc agaagaagat acaccagacg gaagaaccgg atctgctatc tgcaagagat   3840
```

-continued

```
cttcagcaac gagatggcca aggtggacga cagcttcttc cacagactgg aagagtcctt      3900
cctggtggaa gaggataaga agcacgagcg gcaccccatc ttcggcaaca tcgtggacga      3960
ggtggcctac cacgagaagt accccaccat ctaccacctg agaaagaaac tggtggacag      4020
caccgacaag gccgacctgc ggctgatcta tctggccctg gcccacatga tcaagttccg      4080
gggccacttc ctgatcgagg gcgacctgaa ccccgacaac agcgacgtgg acaagctgtt      4140
catccagctg gtgcagacct acaaccagct gttcgaggaa aaccccatca cgccagcgg      4200 cgtggacgcc aaggccatcc tgtctgccag actgagcaag agcagacggc tggaaaatct      4260
gatcgcccag ctgcccggcg agaagaagaa tggcctgttc ggcaacctga ttgccctgag      4320
cctgggcctg accccaact tcaagagcaa cttcgacctg gccgaggatg ccaaactgca      4380
gctgagcaag gacacctacg acgacgacct ggacaacctg ctggcccaga tcggcgacca      4440
gtacgccgac ctgtttctgg ccgccaagaa cctgtccgac gccatcctgc tgagcgacat      4500
cctgagagtg aacaccgaga tcaccaaggc ccccctgagc gcctctatga tcaagagata      4560
cgacgagcac caccaggacc tgaccctgct gaaagctctc gtgcggcagc agctgcctga      4620
gaagtacaaa gagattttct tcgaccagag caagaacggc tacgccggct acatcgatgg      4680
cggagccagc caggaagagt tctacaagtt catcaagccc atcctggaaa agatggacgg      4740
caccgaggaa ctgctcgtga agctgaacag agaggacctg ctgcggaagc agcggacctt      4800
cgacaacggc agcatcccc accagatcca cctgggagag ctgcacgcca ttctgcggcg      4860
gcaggaagat tttacccat tcctgaagga caaccgggaa aagatcgaga agatcctgac      4920
cttccgcatc ccctactacg tgggccctct ggccagggga aacagcagat cgcctggat      4980 gaccagaaag agcgaggaaa ccatcacccc ctggaacttc gaggaagtgg tggacaaggg      5040
cgccagcgcc cagagcttca tcgagcggat gaccaacttc gataagaacc tgcccaacga      5100
gaaggtgctg cccaagcaca gcctgctgta cgagtactt accgtgtaca acagctgac      5160 caaagtgaaa tacgtgaccg agggaatgag aaagcccgcc ttcctgagcg gcgagcagaa      5220
aaaagccatc gtggacctgc tgttcaagac caaccggaaa gtgaccgtga gcagctgaa      5280 agaggactac ttcaagaaaa tcgagtgctt cgactccgtg gaaatctccg gcgtggaaga      5340
tcggttcaac gcctccctgg gcacatacca cgatctgctg aaaattatca aggacaagga      5400
cttcctggac aatgaggaaa acgaggacat tctggaagat atcgtgctga ccctgacact      5460
gtttgaggac agagagatga tcgaggaacg gctgaaaacc tatgcccacc tgttcgacga      5520
caaagtgatg aagcagctga agcggcggag atacaccggc tggggcaggc tgagccggaa      5580
gctgatcaac ggcatccggg acaagcagtc cggcaagaca atcctggatt tcctgaagtc      5640
cgacggcttc gccaacagaa acttcatgca gctgatccac gacgacagcc tgacctttaa      5700
agaggacatc cagaaagccc aggtgtccgg ccagggcgat agcctgcacg agcacattgc      5760
caatctggcc ggcagccccg ccattaagaa gggcatcctg cagacagtga aggtggtgga      5820
cgagctcgtg aaagtgatgg gccggcacaa gcccgagaac atcgtgatcg aaatggccag      5880
agagaaccag accacccaga agggacagaa gaacagccgc gagagaatga gcggatcga      5940 agagggcatc aaagagctgg gcagccagat cctgaaagaa caccccgtgg aaaacaccca      6000
gctgcagaac gagaagctgt acctgtacta cctgcagaat gggcgggata tgtacgtgga      6060
ccaggaactg gacatcaacc ggctgtccga ctacgatgtg gacgctatcg tgcctcagag      6120
ctttctgaag gacgactcca tcgataacaa agtgctgact cggagcgaca agaaccgggg      6180
```

-continued

```
caagagcgac aacgtgccct ccgaagaggt cgtgaagaag atgaagaact actggcgcca    6240
gctgctgaat gccaagctga ttacccagag gaagttcgac aatctgacca aggccgagag    6300
aggcggcctg agcgaactgg ataaggccgg cttcatcaag agacagctgg tggaaacccg    6360
gcagatcaca aagcacgtgg cacagatcct ggactcccgg atgaacacta agtacgacga    6420
gaacgacaaa ctgatccggg aagtgaaagt gatcaccctg aagtccaagc tggtgtccga    6480
tttccggaag gatttccagt tttacaaagt gcgcgagatc aacaactacc accacgccca    6540
cgacgcctac ctgaacgccg tcgtgggaac cgccctgatc aaaaagtacc ctaagctgga    6600
aagcgagttc gtgtacggcg actacaaggt gtacgacgtg cggaagatga tcgccaagag    6660
cgagcaggaa atcggcaagg ctaccgccaa gtacttcttc tacagcaaca tcatgaactt    6720
tttcaagacc gagattaccc tggccaacgg cgagatccgg aagcggcctc tgatcgagac    6780
aaacggcgaa acaggcgaga tcgtgtggga taagggccgg gactttgcca ccgtgcggaa    6840
agtgctgtct atgccccaag tgaatatcgt gaaaaagacc gaggtgcaga caggcggctt    6900
cagcaaagag tctatcctgc ccaagaggaa cagcgacaag ctgatcgcca gaaagaagga    6960
ctgggaccct aagaagtacg gcggcttcga cagccccacc gtggcctatt ctgtgctggt    7020
ggtggccaaa gtggaaaagg gcaagtccaa gaaactgaag agtgtgaaag agctgctggg    7080
gatcaccatc atggaaagaa gcagcttcga gaagaatccc atcgactttc tggaagccaa    7140
gggctacaaa gaagtgaaaa aggacctgat catcaagctg cctaagtact ccctgttcga    7200
gctggaaaac ggccggaaga gaatgctggc ctctgccggc gaactgcaga agggaaacga    7260 actgccctg ccctccaaat atgtgaactt cctgtacctg gccagccact atgagaagct    7320
gaagggctcc cccgaggata tgagcagaa acagctgttt gtggaacagc acaaacacta    7380
cctggacgag atcatcgagc agatcagcga gttctccaag agagtgatcc tggccgacgc    7440
taatctggac aaggtgctga gcgcctacaa caagcacaga gacaagccta tcagagagca    7500
ggccgagaat atcatccacc tgtttaccct gaccaatctg ggagcccctg ccgccttcaa    7560
gtactttgac accaccatcg accggaagag gtacaccagc accaaagagg tgctggacgc    7620
caccctgatc caccagagca tcaccggcct gtacgacaca cggatcgacc tgtctcagct    7680
gggaggcgac gcctatccct atgacgtgcc cgattatgcc agcctgggca gcggctcccc    7740
caagaaaaaa cgcaaggtgg aagatcctaa gaaaaagcgg aaagtggacg cattggtag    7800 tgggagcaac ggcagcagcg gatccagcga gctgattaag gagaacatgc acatgaagct    7860
gtacatggag ggcaccgtgg acaaccatca cttcaagtgc acatccgagg gcgaaggcaa    7920 gcccctacgag ggcacccaga ccatgagaat caaggtggtc gagggcggcc ctctcccctt    7980
cgccttcgac atcctggcta ctagcttcct ctacggcagc aagaccttca tcaaccacac    8040
ccagggcatc cccgacttct tcaagcagtc cttccctgag ggcttcacat gggagagagt    8100
caccacatac gaagacgggg gcgtgctgac cgctacccag gacaccagcc tccaggacgg    8160
ctgcctcatc tacaacgtca agatcagagg ggtgaacttc acatccaacg ccctgtgat    8220 gcagaagaaa acactcggct gggaggcctt caccgagacg ctgtacccccg ctgacggcgg    8280 cctgaaggc agaaacgaca tggccctgaa gctcgtgggc gggagccatc tgatcgcaaa    8340
catcaagacc acatatagat ccaagaaacc cgctaagaac ctcaagatgc ctggcgtcta    8400
ctatgtggac tacagactgg aaagaatcaa ggaggccaac aacgagacct acgtcgagca    8460
gcacgaggtg gcagtggcca gatactgcga cctccctagc aaactggggc acaagcttaa    8520
tggcggtggc ggagggatgg atgctaagtc actaactgcc tggtcccgga cactggtgac    8580
```

```
cttcaaggat gtatttgtgg acttcaccag ggaggagtgg aagctgctgg acactgctca   8640
gcagatcgtg tacagaaatg tgatgctgga gaactataag aacctggttt ccttgggtta   8700
tcagcttact aagccagatg tgatcctccg gttggagaag ggagaagagc cccttgaggg   8760
cagaggaagt ctgctaacat gcggtgacgt ggaggagaat cccggccctg ctagcatgaa   8820
gaagcccgaa ctcaccgcta ccagcgttga aaaatttctc atcgagaagt cgacagtgt   8880 gagcgacctg atgcagttgt cggagggcga agagagccga gccttcagct tcgatgtcgg   8940
cggacgcggc tatgtactgc gggtgaatag ctgcgctgat ggcttctaca aagaccgcta   9000
cgtgtaccgc cacttcgcca gcgctgcact acccatcccc gaagtgttgg acatcggcga   9060
gttcagcgag agcctgacat actgcatcag tagacgcgcc caaggcgtta ctctccaaga   9120
cctccccgaa acagagctgc ctgctgtgtt acagcctgtc gccgaagcta tggatgctat   9180
tgccgccgcc gacctcagtc aaaccagcgg cttcggccca ttcgggcccc aaggcatcgg   9240
ccagtacaca acctggcggg atttcatttg cgccattgct gatccccatg tctaccactg   9300
gcagaccgtg atggacgaca ccgtgtccgc cagcgtagct caagccctgg acgaactgat   9360
gctgtgggcc gaagactgtc ccgaggtgcg ccacctcgtc catgccgact tcggcagcaa   9420
caacgtcctg accgacaacg gccgcatcac cgccgtaatc gactggtccg aagctatgtt   9480
cggggacagt cagtacgagg tggccaacat cttcttctgg cggccctggc tggcttgcat   9540
ggagcagcag actcgctact tcgagcgccg gcatcccgag ctggccggca gccctcgtct   9600
gcgagcctac atgctgcgca tcggcctgga tcagctctac cagagcctcg tggacggcaa   9660
cttcgacgat gctgcctggg ctcaaggccg ctgcgatgcc atcgtccgca gcgggccgg   9720 caccgtcggt cgcacacaaa tcgctcgccg gagcgcagcc gtatggaccg acggctgcgt   9780
cgaggtgctg gccgacagcg gcaaccgccg gcccagtaca cgaccgcgcg ctaaggaggt   9840
aggtcgagtt taaggcccga ctgtgccttc tagttgccag ccatctgttg tttgcccctc   9900
ccccgtgcct tccttgaccc tggaaggtgc cactcccact gtcctttcct aataaaatga   9960
ggaaattgca tcgcattgtc tgagtaggtg tcattctatt ctggggggtg gggtggggca   10020
ggacagcaag ggggaggatt gggaggacaa tagcaggcat gctggggatg cggtgggctc   10080
tatggctgaa aactattccg gaatgggaat ccaggggtag gagatgcttt ggctctagat   10140
gcaagacatg aagcgtttgc ttctggccac caggggagc tgctgggacg cagacggact   10200
ccaaggactg gagccagaag cctggtgttg gtcgagtgta tgtaaacttc tgacccactg   10260
ggaatgtgat gaaagaaata aaagctgaaa tgaatcattc tctctactat tattctgata   10320
tttcacattc ttaaaataaa gtggtgatcc taactgacct aagacaggga atttttacta   10380
ggattaaatg tcaggaattg tgaaaaagtg agtttaaatg tatttggcta aggtgtatgt   10440
aaacttccga cttcaactgt atagaataag agacaacgca cctagctatg ctgaaagcga   10500
gaatccggga aggtctgtac gggcttctgt tatggtgtca acactacgag aagaaaatcg   10560
atcggaattg tcgaatgaag ggaataatgt cgaggcacag acttcaacag caagaaaggt   10620
tctgaatttt ttcaaaagaa ggagcatgag ggtttgatac agttgaagtc ggaagtttac   10680
atacacttaa gttggagtca ttaaaactcg tttttcaact actccacaaa tttcttgtta   10740
acaaacaata gttttggcaa gtcagttagg acatctactt tgtgcatgac acaagtcatt   10800
tttccaacaa ttgtttacag acagattatt tcacttataa ttcactgtat cacaattcca   10860
gtgggtcaga agtttacata cactaagttg actgaaaaaa aaaagaaaa agaaaacacc   10920
```

-continued

```
tactttcctc tccatggaaa cagcatgcca gaaaattttg tggacccttg aaatgagcac  10980
acatctcact tgcaaaagca cagcaccagc gccctctgct gtttcctggt ttgatttaga  11040
actcagagaa gctacagtac tttctagact aaaataccat gtagagttca ggataattat  11100
attctagatt agacataggc atctagagct agcg                              11134
```

<210> SEQ ID NO 3
<211> LENGTH: 11134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gtttaagagc tatgctggaa acagcatagc aagtttaaat aaggctagtc cgttatcaac    60
ttgaaaaagt ggcaccgagt cggtgctttt ttcgaattta aatcggatcc gcggccgcaa   120
tcaacctctg gattacaaaa tttgtgaaag attgactggt attcttaact atgttgctcc   180
ttttacgcta tgtggatacg ctgctttaat gcctttgtat catgcgttaa ctaaacttgt   240
ttattgcagc ttataatggt tacaaataaa gcaatagcat cacaaatttc acaaataaag   300
catttttttc actgcattct agttgtggtt tgtccaaact catcaatgta tcttatcatg   360
tctgtaagag gttccaactt tcaccataat gaaataagat cactaccggg cgtatttttt   420
gagttatcga gattttcagg agctaaggaa gctaaaatga gtattcaaca tttccgtgtc   480
gcccttattc cctttttttgc ggcattttgc cttcctgttt ttgctcaccc agaaacgctg   540
gtgaaagtaa aagatgctga agatcagttg ggtgcacgag tgggttacat cgaactggat   600
ctcaacagcg gtaagatcct tgagagttta cgccccgaag aacgttttcc aatgatgagc   660
acttttaaag ttctgctatg tggcgcggta ttatcccgta ttgacgccgg gcaagagcaa   720
ctcggtcgcc gcatacacta ttctcagaat gacttggttg aatactcacc agtcacagaa   780
aagcatctca cggatggcat gacagtaaga gaattatgca gtgctgccat aaccatgagt   840
gataacactg cggccaactt acttctggca accatcggag gaccgaagga gctaaccgct   900
tttttgcaca acatggggga tcatgtaact cgccttgatc gttgggaacc ggagctgaat   960
gaagccatac caaacgacga gcgtgacacc acgatgcctg tagcaatggc aacaacgttg  1020
cgcaaactat taactggcga actacttact ctagcttccc ggcaacaact gatagactgg  1080
atggaggcgg ataaagttgc aggatcactt ctgcgctcgg ccctcccggc tggctggttt  1140
attgctgata atctggagc cggtgagcgt ggctctcgcg gtatcattgc agcactgggg  1200
ccagatggta gccctcccg catcgtagtt atctacacga cggggagtca ggcaactatg  1260
gatgaacgaa atagacagat cgctgagata ggtgcctcac tgattaagca ttggtaatga  1320
gggccctgag gacctaaatg taatcacctg gctcacttc gggtgggcct ttctgcgttg  1380
ctggcgtttt tccataggct ccgcccccct gacgagcatc acaaaaatcg gtgctcaagt  1440
cagaggtggc gaaacccgac aggactataa agataccagg cgtttccccc tggaagctcc  1500
ctcgtgcgct ctcctgttcc gaccctgccg cttaccggat acctgtccgc ctttctccct  1560
tcgggaagcg tggcgctttc tcatagctca cgctgtaggt atctcagttc ggtgtaggtc  1620
gttcgctcca agctgggctg tgtgcacgaa ccccccgttc agcccgaccg ctgcgcctta  1680
tccggtaact atcgtcttga gtccaacccg gtaagacacg acttatcgcc actggcagca  1740
gccactggta acaggattag cagagcgagg tatgtaggcg gtgctacaga gttcttgaag  1800
```

-continued

```
tggtggccta actacggcta cactagaaga acagtatttg gtatctgcgc tctgctgaag      1860
ccagttacct cggaaaaaga gttggtagct cttgatccgg caaacaaacc accgctggta      1920
gcggtggttt ttttgtttgc aagcagcaga ttacgcgcag aaaaaaagga tctcaagaag      1980
atcctttgat aaggatctgc gatcgctccg gtgcccgtca gtgggcagag cgcacatcgc      2040
ccacagtccc cgagaagttg ggggggaggg tcggcaattg aacgggtgcc tagagaaggt      2100
ggcgcggggt aaactgggaa agtgatgtcg tgtactggct ccgccttttt cccgagggtg      2160
ggggagaacc gtatataagt gcagtagtcg ccgtgaacgt tctttttcgc aacgggtttg      2220
ccgccagaac acagctgaag cttcgagggg ctcgcatctc tccttcacgc gcccgccgcc      2280
ctacctgagg ccgccatcca cgccggttga gtcgcgttct gccgcctccc gcctgtggtg      2340
cctcctgaac tgcgtccgcc gtctaggtaa gtttaaagct caggtcgtga ccgggccttt      2400
gtccggcgct cccttggagc ctacctagac tcagccggct ctccacgctt tgcctgaccc      2460
tgcttgctca actctacgtc tttgtttcgt tttctgttct gcgccgttac agatccaagc      2520
tgtgaccggc gcctacgcta gacgccacca tggacaagaa gtacagcatc ggcctggcca      2580
tcggcaccaa ctctgtgggc tgggccgtga tcaccgacga gtacaaggtg cccagcaaga      2640
aattcaaggt gctgggcaac accgaccggc acagcatcaa gaagaacctg atcggcgccc      2700
tgctgttcga cagcggagaa acagccgagg ccacccggct gaagagaacc gccagaagaa      2760
gatacaccag acggaagaac cggatctgct atctgcaaga gatcttcagc aacgagatgg      2820
ccaaggtgga cgacagcttc ttccacagac tggaagagtc cttcctggtg gaagaggata      2880
agaagcacga gcggcacccc atcttcggca acatcgtgga cgaggtggcc taccacgaga      2940
agtaccccac catctaccac ctgagaaaga aactggtgga cagcaccgac aaggccgacc      3000
tgcggctgat ctatctggcc ctggcccaca tgatcaagtt ccggggccac ttcctgatcg      3060
agggcgacct gaaccccgac aacagcgacg tggacaagct gttcatccag ctggtgcaga      3120
cctacaacca gctgttcgag gaaaacccca tcaacgccag cggcgtggac gccaaggcca      3180
tcctgtctgc cagactgagc aagagcagac ggctggaaaa tctgatcgcc cagctgcccg      3240
gcgagaagaa gaatggcctg ttcggcaacc tgattgccct gagcctgggc ctgaccccca      3300
acttcaagag caacttcgac ctggccgagg atgccaaact gcagctgagc aaggacacct      3360
acgacgacga cctggacaac ctgctggccc agatcggcga ccagtacgcc gacctgtttc      3420
tggccgccaa gaacctgtcc gacgccatcc tgctgagcga catcctgaga gtgaacaccg      3480
agatcaccaa ggcccccctg agcgcctcta tgatcaagag atacgacgag caccaccagg      3540
acctgaccct gctgaaagct ctcgtgcggc agcagctgcc tgagaagtac aaagagattt      3600
tcttcgacca gagcaagaac ggctacgccg gctacatcga tggcggagcc agccaggaag      3660
agttctacaa gttcatcaag cccatcctgg aaaagatgga cggcaccgag gaactgctcg      3720
tgaagctgaa cagagaggac ctgctgcgga agcagcggac cttcgacaac ggcagcatcc      3780
cccaccagat ccacctggga gagctgcacg ccattctgcg gcggcaggaa gattttacc      3840 cattcctgaa ggacaaccgg gaaaagatcg agaagatcct gaccttccgc atcccctact      3900
acgtgggccc tctggccagg ggaaacagca gattcgcctg gatgaccaga aagagcgagg      3960
aaaccatcac cccctggaac ttcgaggaag tggtggacaa gggcgccagc gcccagagct      4020
tcatcgagcg gatgaccaac ttcgataaga acctgcccaa cgagaaggtg ctgcccaagc      4080
acagcctgct gtacgagtac ttcaccgtgt acaacgagct gaccaaagtg aaatacgtga      4140
ccgagggaat gagaaagccc gccttcctga gcggcgagca gaaaaaagcc atcgtggacc      4200
```

-continued

```
tgctgttcaa gaccaaccgg aaagtgaccg tgaagcagct gaaagaggac tacttcaaga    4260
aaatcgagtg cttcgactcc gtggaaatct ccggcgtgga agatcggttc aacgcctccc    4320
tgggcacata ccacgatctg ctgaaaatta tcaaggacaa ggacttcctg gacaatgagg    4380
aaaacgagga cattctggaa gatatcgtgc tgaccctgac actgtttgag gacagagaga    4440
tgatcgagga acggctgaaa acctatgccc acctgttcga cgacaaagtg atgaagcagc    4500
tgaagcggcg gagatacacc ggctgggggca ggctgagccg gaagctgatc aacggcatcc    4560
gggacaagca gtccggcaag acaatcctgg atttcctgaa gtccgacggc ttcgccaaca    4620
gaaacttcat gcagctgatc cacgacgaca gcctgacctt taaagaggac atccagaaag    4680
cccaggtgtc cggccagggc gatagcctgc acgagcacat tgccaatctg gccggcagcc    4740
ccgccattaa gaagggcatc ctgcagacag tgaaggtggt ggacgagctc gtgaaagtga    4800
tgggccggca caagcccgag aacatcgtga tcgaaatggc cagagagaac cagaccaccc    4860
agaagggaca gaagaacagc cgcgagagaa tgaagcggat cgaagagggc atcaaagagc    4920
tgggcagcca gatcctgaaa gaacaccccg tggaaaacac ccagctgcag aacgagaagc    4980
tgtacctgta ctacctgcag aatgggcggg atatgtacgt ggaccaggaa ctggacatca    5040
accggctgtc cgactacgat gtggacgcta tcgtgcctca gagctttctg aaggacgact    5100
ccatcgataa caaagtgctg actcggagcg acaagaaccg gggcaagagc gacaacgtgc    5160
cctccgaaga ggtcgtgaag aagatgaaga actactggcg ccagctgctg aatgccaagc    5220 tgattacccca gaggaagttc gacaatctga ccaaggccga gagaggcggc ctgagcgaac    5280
tggataaggc cggcttcatc aagagacagc tggtggaaac ccggcagatc acaaagcacg    5340
tggcacagat cctggactcc cggatgaaca ctaagtacga cgagaacgac aaactgatcc    5400
gggaagtgaa agtgatcacc ctgaagtcca agctggtgtc cgatttccgg aaggatttcc    5460
agttttacaa agtgcgcgag atcaacaact accaccacgc ccacgacgcc tacctgaacg    5520
ccgtcgtggg aaccgccctg atcaaaaagt accctaagct ggaaagcgag ttcgtgtacg    5580
gcgactacaa ggtgtacgac gtgcggaaga tgatcgccaa gagcgagcag gaaatcggca    5640
aggctaccgc caagtacttc ttctacagca acatcatgaa cttttttcaag accgagatta    5700 ccctggccaa cggcgagatc cggaagcggc ctctgatcga gacaaacggc gaaacaggcg    5760
agatcgtgtg ggataagggc cgggactttg ccaccgtgcg gaaagtgctg tctatgcccc    5820
aagtgaatat cgtgaaaaag accgaggtgc agacaggcgg cttcagcaaa gagtctatcc    5880
tgcccaagag gaacagcgac aagctgatcg ccagaaagaa ggactgggac cctaagaagt    5940
acggcggctt cgacagcccc accgtggcct attctgtgct ggtggtggcc aaagtggaaa    6000
agggcaagtc caagaaactg aagagtgtga aagagctgct ggggatcacc atcatggaaa    6060
gaagcagctt cgagaagaat cccatcgact ttctggaagc caagggctac aaagaagtga    6120
aaaaggacct gatcatcaag ctgcctaagt actccctgtt cgagctggaa aacggccgga    6180
agagaatgct ggcctctgcc ggcgaactgc agaagggaaa cgaactggcc ctgccctcca    6240
aatatgtgaa cttcctgtac ctggccagcc actatgagaa gctgaagggc tcccccgagg    6300
ataatgagca gaaacagctg tttgtggaac agcacaaaca ctacctggac gagatcatcg    6360
agcagatcag cgagttctcc aagagagtga tcctggccga cgctaatctg gacaaggtgc    6420
tgagcgccta caacaagcac agagacaagc ctatcagaga gcaggccgag aatatcatcc    6480
acctgtttac cctgaccaat ctgggagccc ctgccgcctt caagtacttt gacaccacca    6540
```

-continued

```
tcgaccggaa gaggtacacc agcaccaaag aggtgctgga cgccaccctg atccaccaga    6600
gcatcaccgg cctgtacgag acacggatcg acctgtctca gctgggaggc gacgcctatc    6660
cctatgacgt gcccgattat gccagcctgg gcagcggctc ccccaagaaa aaacgcaagg    6720
tggaagatcc taagaaaaag cggaaagtgg acggcattgg tagtgggagc aacggcagca    6780
gcggatccag cgagctgatt aaggagaaca tgcacatgaa gctgtacatg gagggcaccg    6840
tggacaacca tcacttcaag tgcacatccg agggcgaagg caagccctac gagggcaccc    6900
agaccatgag aatcaaggtg gtcgagggcg ccctctccc cttcgccttc gacatcctgg    6960
ctactagctt cctctacggc agcaagacct tcatcaacca cacccagggc atccccgact    7020
tcttcaagca gtccttccct gagggcttca catgggagag agtcaccaca tacgaagacg    7080
ggggcgtgct gaccgctacc caggacacca gcctccagga cggctgcctc atctacaacg    7140
tcaagatcag aggggtgaac ttcacatcca acggccctgt gatgcagaag aaaacactcg    7200
gctgggaggc cttcaccgag acgctgtacc ccgctgacgg cggcctggaa ggcagaaacg    7260
acatggccct gaagctcgtg ggcgggagcc atctgatcgc aaacatcaag accacatata    7320
gatccaagaa accgctaag aacctcaaga tgcctggcgt ctactatgtg gactacagac    7380
tggaaagaat caaggaggcc aacaacgaga cctacgtcga gcagcacgag gtggcagtgg    7440
ccagatactg cgacctccct agcaaactgg ggcacaagct taatggcggt ggcggaggga    7500
tggatgctaa gtcactaact gcctggtccc ggacactggt gaccttcaag gatgtatttg    7560
tggacttcac cagggaggag tggaagctgc tggacactgc tcagcagatc gtgtacagaa    7620
atgtgatgct ggagaactat aagaacctgg tttccttggg ttatcagctt actaagccag    7680
atgtgatcct ccggttggag aagggagaag agccccttga gggcagagga agtctgctaa    7740
catgcggtga cgtggaggag aatcccggcc ctgctagcat gaagaagccc gaactcaccg    7800
ctaccagcgt tgaaaaattt ctcatcgaga agttcgacag tgtgagcgac ctgatgcagt    7860
tgtcggaggg cgaagagagc cgagccttca gcttcgatgt cggcggacgc ggctatgtac    7920
tgcgggtgaa tagctgcgct gatggcttct acaaagaccg ctacgtgtac cgccacttcg    7980
ccagcgctgc actacccatc cccgaagtgt tggacatcgg cgagttcagc gagagcctga    8040
catactgcat cagtagacgc gcccaaggcg ttactctcca agacctcccc gaaacagagc    8100
tgcctgctgt gttacagcct gtcgccgaag ctatggatgc tattgccgcc gccgacctca    8160
gtcaaaccag cggcttcggc ccattcgggc cccaaggcat cggccagtac acaacctggc    8220
gggatttcat ttgcgccatt gctgatcccc atgtctacca ctggcagacc gtgatggacg    8280
acaccgtgtc cgccagcgta gctcaagccc tggacgaact gatgctgtgg gccgaagact    8340
gtcccgaggt gcgccacctc gtccatgccg acttcggcag caacaacgtc ctgaccgaca    8400
acggccgcat caccgccgta atcgactggt ccgaagctat gttcggggac agtcagtacg    8460
aggtggccaa catcttcttc tggcggccct ggctggcttg catggagcag cagactcgct    8520
acttcgagcg ccggcatccc gagctggccg gcagccctcg tctgcgagcc tacatgctgc    8580
gcatcggcct ggatcagctc taccagagcc tcgtggacgg caacttcgac gatgctgcct    8640
gggctcaagg ccgctgcgat gccatcgtcc gcagcggggc cggcaccgtc ggtcgcacac    8700
aaatcgctcg ccggagcgca gccgtatgga ccgacggctg cgtcgaggtg ctggccgaca    8760
gcggcaaccg ccggcccagt acacgaccgc gcgctaagga ggtaggtcga gtttaaggcc    8820
cgactgtgcc ttctagttgc cagccatctg ttgtttgccc ctcccccgtg ccttccttga    8880
ccctggaagg tgccactccc actgtccttt cctaataaaa tgaggaaatt gcatcgcatt    8940
```

-continued

```
gtctgagtag gtgtcattct attctggggg gtggggtggg gcaggacagc aaggggaggg   9000
attgggagga caatagcagg catgctgggg atgcggtggg ctctatggct gaaaactatt   9060
ccggaatggg aatccagggg taggagatgc tttggctcta gatgcaagac atgaagcgtt   9120
tgcttctggc caccaggggg agctgctggg acgcagacgg actccaagga ctggagccag   9180
aagcctggtg ttggtcgagt gtatgtaaac ttctgaccca ctgggaatgt gatgaaagaa   9240
ataaaagctg aaatgaatca ttctctctac tattattctg atatttcaca ttcttaaaat   9300
aaagtggtga tcctaactga cctaagacag ggaattttta ctaggattaa atgtcaggaa   9360
ttgtgaaaaa gtgagtttaa atgtatttgg ctaaggtgta tgtaaacttc cgacttcaac   9420
tgtatagaat aagagacaac gcacctagct atgctgaaag cgagaatccg ggaaggtctg   9480
tacgggcttc tgttatggtg tcaacactac gagaagaaaa tcgatcggaa ttgtcgaatg   9540
aagggaataa tgtcgaggca cagacttcaa cagcaagaaa ggttctgaat tttttcaaaa   9600
gaaggagcat gagggtttga tacagttgaa gtcggaagtt tacatacact taagttggag   9660
tcattaaaac tcgtttttca actactccac aaatttcttg ttaacaaaca atagttttgg   9720
caagtcagtt aggacatcta ctttgtgcat gacacaagtc attttccaa caattgttta    9780 cagacagatt atttcactta taattcactg tatcacaatt ccagtgggtc agaagtttac   9840
atacactaag ttgactgaaa aaaaaaaga aaagaaaac acctactttc tctccatgg     9900 aaacagcatg ccagaaaatt ttgtggaccc ttgaaatgag cacacatctc acttgcaaaa   9960
gcacagcacc agcgccctct gctgtttcct ggtttgattt agaactcaga gaagctacag   10020
tactttctag actaaaatac catgtagagt tcaggataat tatattctag attagacata   10080
ggcatctaga gctagcggag ggcctatttc ccatgattcc ttcatatttg catatacgat   10140
acaaggctgt tagagagata attagaatta atttgactgt aaacacaaag atattagtac   10200
aaaatacgtg acgtagaaag taataatttc ttgggtagtt tgcagtttta aaattatgtt   10260
ttaaaatgga ctatcatatg cttaccgtaa cttgaaagta tttcgatttc ttggctttat   10320
atatcttgtg gaaaggacga aaggagccag ccgagtccgg gctgtttaag agctatgctg   10380
gaaacagcat agcaagttta aataaggcta gtccgttatc aacttgaaaa agtggcaccg   10440
agtcggtgct ttttttgaacg ctgacgtcat caacccgctc caaggaatcg cgggcccagt   10500
gtcactaggc gggaacaccc agcgcgcgtg cgccctggca ggaagatggc tgtgagggac   10560
aggggagtgg cgccctgcaa tatttgcatg tcgctatgtg ttctgggaaa tcaccataaa   10620
cgtgaaatgt ctttggattt gggaatctta taagttctgt atgagaccac tctttcccag   10680
cgagggctgg gagatccgtg tttaagagct atgctggaaa cagcatagca agtttaaata   10740
aggctagtcc gttatcaact tgaaaaagt gcaccgagtc ggtgcttttt ttctagagat   10800
ccgacgccgc catctctagg cccgcgccgg cccctcgca cagacttgtg ggagaagctc    10860
ggctactccc ctgccccggt taatttgcat ataatatttc ctagtaacta tagaggctta   10920
atgtgcgata aaagacagat aatctgttct tttttaatact agctacattt tacatgatag   10980
gcttggattt ctataagaga tacaaatact aaattattat tttaaaaaac agcacaaaag   11040
gaaactcacc ctaactgtaa agtaattgtg tgttttgaga ctataaatat gcatgcgaga   11100
aaagccttgt ttgggccctg gggctgaggc tcag                              11134
```

<210> SEQ ID NO 4
<211> LENGTH: 9557
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 4

```
ttaaccctag aaagataatc atattgtgac gtacgttaaa gataatcatg tgtaaaattg     60
acgcatgtga ctgaaaaaaa aaaagaaaaa gaaaacacct actttcctct ccatggaaac    120
agcatgccag aaaattttgt ggacccttga aatgagcaca catctcactt gcaaaagcac    180
agcaccagcg ccctctgctg tttcctggtt tgatttagaa ctcagagaag ctacagtact    240
ttctagacta aaataccatg tagagttcag gataattata ttctagatta gacataggca    300
agactagtta ttaatagtaa tcaattacgg ggtcattagt tcatagccca tatatggagt    360
tccgcgttac ataacttacg gtaaatggcc cgcctggctg accgcccaac gacccccgcc    420
cattgacgtc aataatgacg tatgttccca tagtaacgcc aatagggact ttccattgac    480
gtcaatgggt ggagtattta cggtaaactg cccacttggc agtacatcaa gtgtatcata    540
tgccaagtcc gcccctatt gacgtcaatg acggtaaatg gcccgcctgg cattatgccc    600
agtacatgac cttacgggac tttcctactt ggcagtacat ctacgtatta gtcatcgcta    660
ttaccatggt gatgcggttt tggcagtaca ccaatgggcg tggatagcgg tttgactcac    720
ggggatttcc aagtctccac cccattgacg tcaatgggag tttgttttgg caccaaaatc    780
aacgggactt tccaaaatgt cgtaatacc ccgccccgtt gacgcaaatg ggcaagcttg    840
ccgggtcgag gtaggcgtgt acggtgggag gcctatataa gcaaccggta taatcaaaca    900
gaccagattg tctgtttgtt accggtgttt agtgaaccgg gcgcgcctca tatcgcctgg    960
agacgccatc cacgctgttt tgacctccat agaagacacc gggaccgatc cagcctccgc   1020
ggtcactctc ttccgcatcg ctgtctgcga gggccagctg ttgggctcgc ggttgaggac   1080
aaactcttcg cggtctttcc agtactcttg gatcggaaac ccgtcggcct ccgaacggta   1140
ctccgccacc gagggacctg agcgagtccg catcgaccgg atcggaaaac ctctcgagaa   1200
aggcgtctaa ccagtcacag tcgcaaggta ggctgagcac cgtggcgggc ggcagcgggt   1260
ggcggtcggg gttgtttctg gcggaggtgc tgctgatgat gtaattaaag taggcggtct   1320
tgagacggcg gatggtcgag gtgaggtgtg gcaggcttga gatccagctg ttggggtgag   1380
tactccctct caaaagcggg cattacttct gcgctaagat tgtcagtttc caaaaacgag   1440
gaggatttga tattcacctg cccgatctg gccatacact tgagtgacaa tgacatccac   1500
tttgcctttc tctccacagg tgtccactcc caggtccaag tttggtctag acacttgaca   1560
gccaccatgt catggtttag tggactcctg gtccctaaag tggatgaacg aaaacagcc   1620 tggggtgaac gaaatggaca gaagcgttcg agaaggcgtg gcactagggc aggtggattc   1680
tgcacgcctc gctatatgag ctgcctcaga gatgcagagc cacccagccc aaccccctgct   1740 ggaccaccta gatgcccttg gcaggatgac gccttcatca gaagggggagg accaggtaag   1800 ggtaaggagt tgggtctgag agcagtggct ctgggtttcg aggataccga ggtgacaacg   1860
acagcaggag gtacggctga ggtggcacct gacgcagtgc ccaggagtgg gcgatcctgc   1920
tggagacgtc tggtgcaggt gttccagtcg aagcagttcc gttcggccaa gctggagcgc   1980
ctgtaccagc ggtacttctt ccagatgaac cagagcagcc tgacgctgct gatggcggtg   2040
ctggtgctgc tcacagcggt gctgctggct ttccacgctg cacctgctcg ccctcagcct   2100
gcttatgtgg cactgttggc ctgtgcagca gcactgttcg tgggactcat ggtggtgtgt   2160
```

-continued

```
aacagacata gcttcagaca ggactccatg tgggtggtga gctacgtggt gctgggcatc   2220
ctggcagcag tgcaggtcgg aggagcactc gcagcagacc ctcgcagccc ctctgcggga   2280
ctctggtgcc ctgtgttctt tgtctacatc gcctacacgc tcctccccat ccgcatgaga   2340
gctgccgtcc tcagcggact gggactctcc accttgcatt tgatcttggc ctggcaactt   2400
aaccgtggtg atgccttcct ctggaagcag ctcggtgcca atgtgctgct gttcctctgc   2460
accaacgtca ttggcatctg cacacactat ccagcagagg tgtctcagcg ccaggccttt   2520
caggagaccc gcggttacat ccaggcccgg ctccacctgc agcatgagaa tcggcagcag   2580
gagcggctgc tgctgtcggt attgccccag cacgttgcca tggagatgaa agaagacatc   2640
aacacaaaaa aagaagacat gatgttccac aagatctaca tacagaagca tgacaatgtc   2700
agcatcctgt ttgcagacat tgagggcttc accagcctgg catcccagtg cactgcgcag   2760
gagctggtca tgaccctgaa tgagctgttt gcccggtttg acaagctggc tgcggagaat   2820
cactgcctga ggatcaagat cttgggggac tgttactact gtgtgtcagg gctgccggag   2880
gcccgggccg accatgccca ctgctgtgtg gagatggggg tagacatgat tgaggccatc   2940
tcgctggtac gtgaggtgac aggtgtgaat gtgaacatgc gcgtgggcat ccacagcggg   3000
cgcgtgcact gcggcgtcct tggcttgcgg aaatggcagt tcgatgtgtg gtccaatgat   3060
gtgaccctgg ccaaccacat ggaggcagga ggccgggctg gccgcatcca catcactcgg   3120
gcaacactgc agtacctgaa cggggactac gaggtggagc caggccgtgg tggcgagcgc   3180
aatgcgtacc tcaaggagca gcacattgag actttcctca tcctgggcgc cagccagaaa   3240
cggaaagagg agaaggccat gctggccaag ctgcagcgga ctcgggccaa ctccatggaa   3300
gggctgatgc cgcgctgggt tcctgatcgt gccttctccc ggaccaagga ctccaaggcc   3360
ttccgccaga tgggcattga tgattccagc aaagacaacc ggggcaccca agatgccctg   3420
aaccctgagg atgaggtgga tgagttcctg agccgtgcca tcgacgcccg cagcattgat   3480
cagctgcgga aggaccatgt gcgccggttt ctgctcacct tccagagaga ggatcttgag   3540
aagaagtact cccggaaggt cgatccccgc ttcggagcct acgttgcctg tgccctgttg   3600
gtcttctgct tcatctgctt catccagctt ctcatcttcc cacactccac cctgatgctt   3660
gggatctatg ccagcatctt cctgctgctg ctaatcaccg tgctgatctg tgctgtgtac   3720
tcctgtggtt ctctgttccc taaggccctg caacgtctgt cccgcagcat tgtccgctca   3780
cgggcacata gcaccgcagt tggcatcttt tccgtcctgc ttgtgtttac ttctgccatt   3840
gccaacatgt tcacctgtaa ccacacccct atacggagct gtgcagcccg gatgctgaat   3900
ttaacacctg ctgacatcac tgcctgccac ctgcagcagc tcaattactc tctgggcctg   3960
gatgctcccc tgtgtgaggg caccatgccc acctgcagct ttcctgagta cttcatcggg   4020
aacatgctgc tgagtctctt ggccagctct gtcttcctgc acatcagcag catcgggaag   4080
ttggccatga tctttgtctt ggggctcatc tatttggtgc tgcttctgct gggtcccccca   4140 gccaccatct ttgacaacta tgacctactg cttggcgtcc atggcttggc ttcttccaat   4200
gagacctttg atgggctgga ctgtccagct gcagggaggg tggccctcaa atatatgacc   4260
cctgtgattc tgctggtgtt tgcgctggcg ctgtatctgc atgctcagca ggtggagagc   4320
actgcccgcc tagacttcct ctggaaacta caggcaacag gggagaagga ggagatggag   4380
gagctacagg catacaaccg gaggctgctg cataacattc tgcccaagga cgtggcggcc   4440
cacttcctgg cccgggagcg ccgcaatgat gaactctact atcagtcgtg tgagtgtgtg   4500
gctgttatgt ttgcctccat tgccaacttc tctgagttct atgtggagct ggaggcaaac   4560
```

-continued

```
aatgagggtg tcgagtgcct gcggctgctc aacgagatca tcgctgactt tgatgagatt    4620
atcagcgagg agcggttccg gcagctggaa aagatcaaga cgattggtag cacctacatg    4680
gctgcctcag ggctgaacgc cagcacctac gatcaggtgg gccgctccca catcactgcc    4740
ctggctgact acgccatgcg gctcatggag cagatgaagc acatcaatga gcactccttc    4800
aacaatttcc agatgaagat tgggctgaac atgggcccag tcgtggcagg tgtcatcggg    4860
gctcggaagc cacagtatga catctggggg aacacagtga atgtctctag tcgtatggac    4920
agcacggggg tccccgaccg aatccaggtg accacggacc tgtaccaggt tctagctgcc    4980
aagggctacc agctggagtg tcgaggggtg gtcaaggtga agggcaaggg ggagatgacc    5040
acctacttcc tcaatggggg ccccagcagt taagaatcaa cctctggatt acaaaatttg    5100
tgaaagattg actggtattc ttaactatgt tgctcctttt acgctatgtg gatacgctgc    5160
tttaatgcct ttgtatcatg cgttaactaa acttgtttat tgcagcttat aatggttaca    5220
aataaagcaa tagcatcaca aatttcacaa ataaagcatt tttttcactg cattctagtt    5280
gtggtttgtc caaactcatc aatgtatctt atcatgtctg taagaggttc caactttcac    5340
cataatgaaa taagatcact accgggcgta ttttttgagt tatcgagatt ttcaggagct    5400
aaggaagcta aaatgagtat tcaacatttc cgtgtcgccc ttattccctt ttttgcggca    5460
ttttgccttc ctgtttttgc tcacccagaa acgctggtga agtaaaaga tgctgaagat    5520 cagttgggtg cacgagtggg ttacatcgaa ctggatctca acagcggtaa gatccttgag    5580
agtttacgcc ccgaagaacg ttttccaatg atgagcactt ttaaagttct gctatgtggc    5640
gcggtattat cccgtattga cgccgggcaa gagcaactcg gtcgccgcat acactattct    5700
cagaatgact tggttgaata ctcaccagtc acagaaaagc atctcacgga tggcatgaca    5760
gtaagagaat tatgcagtgc tgccataacc atgagtgata acactgcggc caacttactt    5820
ctggcaacca tcggaggacc gaaggagcta accgcttttt tgcacaacat gggggatcat    5880
gtaactcgcc ttgatcgttg ggaaccggag ctgaatgaag ccataccaaa cgacgagcgt    5940
gacaccacga tgcctgtagc aatggcaaca acgttgcgca aactattaac tggcgaacta    6000
cttactctag cttcccggca acaactgata gactggatgg aggcggataa agttgcagga    6060
tcacttctgc gctcggccct cccggctggc tggtttattg ctgataaatc tggagccggt    6120
gagcgtggct ctcgcggtat cattgcagca ctggggccag atggtaagcc ctcccgcatc    6180
gtagttatct acacgacggg gagtcaggca actatggatg aacgaaatag acagatcgct    6240
gagataggtg cctcactgat taagcattgg taatgagggc cctgaggacc taaatgtaat    6300
cacctggctc accttcgggt gggcctttct gcgttgctgg cgtttttcca taggctccgc    6360
ccccctgacg agcatcacaa aaatcggtgc tcaagtcaga ggtggcgaaa cccgacagga    6420
ctataaagat accaggcgtt tccccctgga agctccctcg tgcgctctcc tgttccgacc    6480
ctgccgctta ccggatacct gtccgccttt ctcccttcgg gaagcgtggc gctttctcat    6540
agctcacgct gtaggtatct cagttcggtg taggtcgttc gctccaagct gggctgtgtg    6600
cacgaacccc ccgttcagcc cgaccgctgc gccttatccg gtaactatcg tcttgagtcc    6660
aacccggtaa gacacgactt atcgccactg gcagcagcca ctggtaacag gattagcaga    6720
gcgaggtatg taggcggtgc tacagagttc ttgaagtggt ggcctaacta cggctacact    6780
agaagaacag tatttggtat ctgcgctctg ctgaagccag ttacctcgga aaaagagttg    6840
gtagctcttg atccggcaaa caaaccaccg ctggtagcgg tggttttttt gtttgcaagc    6900
```

-continued

```
agcagattac gcgcagaaaa aaaggatctc aagaagatcc tttgataagg atctgcgatc   6960
gctccggtgc ccgtcagtgg gcagagcgca catcgcccac agtccccgag aagttggggg   7020
gaggggtcgg caattgaacg ggtgcctaga gaaggtggcg cggggtaaac tgggaaagtg   7080
atgtcgtgta ctggctccgc cttttttcccg agggtggggg agaaccgtat ataagtgcag   7140
tagtcgccgt gaacgttctt tttcgcaacg ggtttgccgc cagaacacag ctgaagcttc   7200 gagggggctcg catctctcct tcacgcgccc gccgccctac ctgaggccgc catccacgcc   7260
ggttgagtcg cgttctgccg cctcccgcct gtggtgcctc ctgaactgcg tccgccgtct   7320
aggtaagttt aaagctcagg tcgtgaccgg gcctttgtcc ggcgctccct tggagcctac   7380
ctagactcag ccggctctcc acgctttgcc tgaccctgct tgctcaactc tacgtctttg   7440
tttcgttttc tgttctgcgc cgttacagat ccaagctgtg accggcgcct acgctagacg   7500
ccaccatggc ttacccatac gatgttccag attacgctag tttggtgagg cagcagagac   7560
cgatgacatc cactttgcct ttctctccac aggtgtccac tcccaggtcc aagtttggaa   7620
gatctaccat gccaaagaga cccagacccg tgatcatgag tccaaagaga agaacacagg   7680
cagagcgcgc aatggagacc cagggcaagt tgattgcagc ggccctgggg gttttacggg   7740
aaaaaggtta cgcgggattc cggatcgcag atgtgcccgg tgctgcaggt gtctcgagag   7800
gagcgcagag ccatcatttc ccgacaaagc ttgagcttct gcttgccact tttgaatggc   7860
tttacgaaca gatcaccgaa cgcagtcggg ctcgattagc gaaattgaag ccagaggatg   7920
acgtcatcca gcaaatgctg gacgacgccg ccgaattttt cctcgacgat gacttctcta   7980
tcagccttga tttgattgtg gctgccgacc gggatccagc gttacgcgag ggtattcagc   8040
gcacggtaga gaggaatcgg tttgtcgtcg aggatatgtg gcttggtgtt ctggtgagcc   8100
gtggtctttc gcgtgatgat gcagaagata tcctttggtt gatattcaat tcggtgcgtg   8160
ggcttgctgt tcgtagccta tggcagaagg acaaagaacg ctttgagcgt gtcaggaact   8220
cgacactcga aattgcgcga gagcggtacg cgaaattcaa gcgcgcggcc aaaccctctg   8280
gcgcggccgc ggagggcaga ggaagtcttc taacatgcgg tgacgtggag gagaatcccg   8340
gccctatgac cgagtacaag cccacggtgc gcctcgccac ccgcgacgac gtccccaggg   8400
ccgtacgcac cctcgccgcc gcgttcgccg actaccccgc cacgcgccac accgtcgatc   8460
cggaccgcca catcgagcgg gtcaccgagc tgcaagaact cttcctcacg cgcgtcgggc   8520
tcgacatcgg caaggtgtgg gtcgcggacg acggcgccgc ggtggcggtc tggaccacgc   8580
cggagagcgt cgaagcgggg gcggtgttcg ccgagatcgg cccgcgcatg gccgagttga   8640
gcggttcccg gctggccgcg cagcaacaga tggaaggcct cctggcgccg caccggccca   8700
aggagcccgc gtggttcctg gccaccgtcg gcgtgtcgcc cgaccaccag ggcaagggtc   8760
tgggcagcgc cgtcgtgctc cccggagtgg aggcggccga gcgcgccggg gtgcccgcct   8820
tcctggaaac ctccgcgccc cgcaacctcc ccttctacga gcggctcggc ttcaccgtca   8880
ccgccgacgt cgaggtgccc gaaggaccgc gcacctggtg catgacccgc aagcccggtg   8940
cctgaggccc gactgtgcct tctagttgcc agccatctgt tgtttgcccc tccccgtgc    9000 cttccttgac cctggaaggt gccactccca ctgtcctttc ctaataaaat gaggaaattg   9060
catcgcattg tctgagtagg tgtcattcta ttctgggggg tggggtgggg caggacagca   9120
agggggagga ttgggaggac aatagcaggc atgctgggga tgcggtgggc tctatggctg   9180
aaaactattc cggaatggga atccaggggt aggagatgct ttggctctag atgcaagaca   9240
tgaagcgttt gcttctggcc accagggggga gctgctggga cgcagacgga ctccaaggac   9300
```

-continued

```
tggagccaga agcctggtgt tgcatgcgtc aattttacgc agactatctt tctagggtta   9360
atagaataag agacaacgca cctagctatg ctgaaagcga gaatccggga aggtctgtac   9420
gggcttctgt tatggtgtca acactacgag aagaaaatcg atcggaattg tcgaatgaag   9480
ggaataatgt cgaggcacag acttcaacag caagaaaggt tctgaatttt ttcaaaagaa   9540
ggagcatgag ggtttga                                                    9557
```

SYSTEMS AND METHODS FOR MEASURING CELL SIGNALING PROTEIN ACTIVITY

CROSS REFERENCE

This application claims the benefit of U.S. Provisional Application No. 63/144,766 filed Feb. 2, 2021, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 24, 2021, is named 52652-708_201_SL.txt and is 56,814 bytes in size.

BACKGROUND

Measuring cellular signaling pathway responses is one of the cornerstones of modern medicine. Cellular signaling pathway responses can stem from innate cellular activity. Cellular signaling pathway responses can be stimulated by exogenous sources such as contacting a cell with a ligand which binds to a receptor expressed on the surface of the cell. The contacting between the ligand and the cell surface receptor initiates changes in enzymatic activities comprising signaling cascades within the cell that leads to changes in cellular signaling pathway responses. As such, measuring or screening enzymatic activities can capture the changes in cellular signaling pathway responses initiated by the ligand contacting the cell surface receptor.

SUMMARY

Described herein are systems and methods for interrogating and measuring cell signaling pathway responses, screening for antagonists, inverse agonists or agonists of cell signaling pathways, or discovering novel cell signaling pathways. Currently methods utilize endogenous response element regulated promoters proximal to nucleic acids encoding reporter molecules. These methods suffer from high degrees of background signal of the reporter molecules due to the "leaky" nature of the endogenous response element binding promoters in cells. Also, these methods suffer from high degrees of: coefficient of variation, false positive, or false negative in measurable activities of cell signaling pathways. Finally, such methods suffer from low absolute values of reporter activation resulting in low ratio of measurable cell signaling activity to background.

In an aspect, the systems and methods described herein comprise at least one nucleic acid encoding a regulatory element and/or an effector of the cell signaling pathway. In some cases, the regulatory element upregulates or downregulates expression of an effector. In some cases, the regulatory element upregulates or downregulates expression of an exogenous effector. In some cases, the regulatory element upregulates or downregulates expression of an endogenous effector. By modulating the expression of the effector, the systems and methods increase measurable cell signaling pathway responses; increases a ratio of measurable cell signaling pathway response to background; and decreases coefficient of variation, false positive, or false negative of the measurable cell signaling pathway.

Described herein, in some embodiments, is a system for measuring G protein-coupled receptor (GPCR) activity in a mammalian cell, the system comprising: a first effector of GPCR activity, where an expression of the first effector of GPCR activity is upregulated compared to an expression of the first effector of GPCR activity in a wild-type state; and a second effector of GPCR activity, where an expression of the second effector of GPCR activity is downregulated compared to an expression of the second effector of GPCR activity in a wild-type state. In some embodiments, the GPCR activity comprises a Gi alpha subunit activity, a Gs alpha subunit activity, a Gq alpha subunit activity, or a G12/13 alpha subunit activity. In some embodiments, the Gi alpha subunit activity comprises activity of G$\alpha$i1, G$\alpha$i2, G$\alpha$i3, G$\alpha$o, G$\alpha$t, G$\alpha$g, or G$\alpha$z. In some embodiments, the GPCR activity comprises the Gs alpha subunit activity, the Gq alpha subunit activity, or the G12/13 alpha subunit activity. In some embodiments, the first effector of GPCR activity comprises a first adenylyl cyclase. In some embodiments, the first adenylyl cyclase is selected from the group consisting of ADCY1, ADCY2, ADCY3, ADCY4, ADCY5, ADCY6, ADCY7, ADCY8, ADCY9, and ADCY10. In some embodiments, the first adenylyl cyclase is ADCY6. In some embodiments, the first adenylyl cyclase is encoded by a nucleic acid operatively coupled to a promoter or enhancer that overexpresses the first adenylyl cyclase compared to a wild-type state. In some embodiments, the second effector of GPCR activity comprises a second adenylyl cyclase. In some embodiments, the second adenylyl cyclase is selected from the group consisting of ADCY1, ADCY2, ADCY3, ADCY4, ADCY5, ADCY6, ADCY7, ADCY8, ADCY9, and ADCY10. In some embodiments, the second adenylyl cyclase is ADCY3. In some embodiments, the second adenylyl cyclase is targeted by one or more of a microRNA, an shRNA, an siRNA, a CRISPR/Cas9 complex that reduces expression of the second adenylyl cyclase compared to a wild-type state. In some embodiments, the system comprises a reporter nucleic acid, where the reporter nucleic acid generates a detectable signal from a reporter gene that is proportional to the GPCR activity. In some embodiments, the reporter nucleic acid comprises a cAMP response element (CRE) sequence operatively coupled to the reporter gene. In some embodiments, the reporter gene comprises a unique molecular identifier (UMI) nucleic acid sequence. In some embodiments, the reporter gene comprises one or more of: an expression of a unique molecular identifier, a fluorescent signal, a luminescent signal. In some embodiments, the mammalian cell is selected from the group consisting of a HEK 293 cell, a CHO-K1 cell, a COS-7 cell, and an U2OS cell. In some embodiments, the system is integrated into a genome of the mammalian cell.

Described herein, in some embodiments, is a method for measuring the GPCR activity in a cell, the method comprising contacting a system described herein with a GPCR ligand, where the ligand complexes with the GPCR and initiates or inhibits the GPCR activity. In some embodiments, the GPCR ligand is selected from the group consisting of a polypeptide and a small molecule.

In one aspect described herein is a system for measuring G protein-coupled receptor (GPCR) activity, the system comprising: (a) a first effector of the GPCR activity, where an expression of the first effector is upregulated compared to an expression of the first effector in a wild-type state; and (b) a second effector of the GPCR activity, where an expression of the second effector is downregulated compared to an expression of the second effector in a wild-type state. In certain embodiments, the expression of the first effector is upregulated by contacting a GPCR with a GPCR activator. In certain embodiments, the GPCR activator is a GPCR agonist. In certain embodiments, the GPCR activator is an agonist of the first effector. In certain embodiments, the system comprises a first nucleic acid encoding the first effector of the GPCR activity is operably coupled to a regulatory element for upregulating expression of the first effector. In certain embodiments, the expression of the second effector is downregulated by contacting a GPCR with a GPCR inhibitor. In certain embodiments, the GPCR inhibitor is a GPCR inverse agonist. In certain embodiments, the GPCR inhibitor is a GPCR antagonist. In certain embodiments, the GPCR inhibitor is an inverse agonist of the second effector. In certain embodiments, the GPCR inhibitor is an antagonist of the second effector. In certain embodiments, the system comprises a second nucleic acid that downregulates the expression of the second effector. In certain embodiments, the GPCR activity comprises a $G_i$ alpha subunit activity, a $G_s$ alpha subunit activity, a $G_q$ alpha subunit activity, or a $G_{12/13}$ alpha subunit activity. In certain embodiments, the GPCR activity comprises the $G_i$ alpha subunit activity. In certain embodiments, the $G_i$ alpha subunit activity comprises activity of Gαi1, Gαi2, Gαi3, Gαo, Gαt, Gαg or Gαz. In certain embodiments, the GPCR activity comprises the Gs alpha subunit activity. In certain embodiments, the GPCR activity comprises the $G_q$ alpha subunit activity. In certain embodiments, the GPCR activity comprises the $G_{12/13}$ alpha subunit activity. In certain embodiments, the regulatory element is inducible. In certain embodiments, the regulatory element is constitutively active. In certain embodiments, the first effector comprises a first adenylyl cyclase. In certain embodiments, the first adenylyl cyclase is selected from the group consisting of ADCY1, ADCY2, ADCY3, ADCY4, ADCY5, ADCY6, ADCY7, ADCY8, ADCY9, and ADCY10. In certain embodiments, the first adenylyl cyclase is ADCY6. In certain embodiments, the second effector comprises a second adenylyl cyclase. In certain embodiments, the second adenylyl cyclase is selected from the group consisting of ADCY1, ADCY2, ADCY3, ADCY4, ADCY5, ADCY6, ADCY7, ADCY8, ADCY9, and ADCY10. In certain embodiments, the second adenylyl cyclase is ADCY3. In certain embodiments, the second nucleic acid comprises a microRNA, a shRNA, a siRNA, a gRNA, or a combination thereof. In certain embodiments, the second nucleic acid comprises the microRNA. In certain embodiments, the second nucleic acid comprises the gRNA. In certain embodiments, the system further comprises a CRISPR-Cas system operatively coupled to the gRNA. In certain embodiments, the GPCR activity comprises cyclic AMP (cAMP) activity. In certain embodiments, the GPCR activity comprises a change in cAMP concentration. In certain embodiments, the GPCR activity comprises an inverse cAMP activity. In certain embodiments, the system increases the cAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a cAMP activity in a cell without the system. In certain embodiments, the system increases the cAMP concentration in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a cAMP concentration in a cell without the system. In certain embodiments, the system increases the inverse cAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to an inverse cAMP activity in a cell without the system. In certain embodiments, the system comprises a second regulatory element for upregulating expression of a $G_i$ alpha subunit. In certain embodiments, the system comprises at least one additional effector. In certain embodiments, the at least one additional effector is an adenylyl cyclase. In certain embodiments, the system further comprises a second regulatory element for upregulating expression of the at least one additional effector. In certain embodiments, the system increases a ratio between the GPCR activity and a background in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a ratio between the GPCR activity and the background in a cell without the system. In certain embodiments, the system increases the GPCR activity in the cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the GPCR activity in the cell without the system. In certain embodiments, the system decreases the background in the cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the background in the cell without the system. In certain embodiments, the system comprises a reporter nucleic acid, where the reporter nucleic acid generates a detectable signal that is proportional to the GPCR activity. In certain embodiments, the reporter nucleic acid comprises a cAMP response element (CRE) sequence. In certain embodiments, the reporter nucleic acid is operatively coupled to an unique molecular identifier (UMI) nucleic acid sequence. In certain embodiments, the detectable signal comprises a fluorescent signal. In certain embodiments, the detectable signal comprises a luminescent signal. In certain embodiments, the first nucleic acid comprises a gene expression cassette for upregulating the expression of the first effector. In certain embodiments, the second nucleic acid comprises a gene expression cassette for downregulating the expression of the second effector. Also described herein is a cell comprises the system described. In certain embodiments, the cell comprises an eukaryotic cell. In certain embodiments, the cell is a mammalian cell. In certain embodiments, the is a mammalian cell-derived cell. In certain embodiments, the cell is derived from a cell line. In certain embodiments, the cell is selected from the group consisting of a CHO-K1 cell, a COS-7 cell, and an U2OS cell. In certain embodiments, the system is integrated into a genome of the cell. In certain embodiments, the cell comprises a cell population. In certain embodiments, the cell population comprises a population of eukaryotic cells. In certain embodiments, the cell population comprises a population of mammalian cells. In certain embodiments, the cell population comprises a population mammalian cell-derived cells. In certain embodiments, the cell population comprises a population of cells derived from a cell line. In certain embodiments, the cell population comprises a population of cells selected from the group consisting of CHO-K1 cells, COS-7 cells, and U2OS cells. Also described herein is a method for measuring the GPCR activity comprises measuring the GPCR activity in the cell or the cell population. In certain embodiments, the GPCR activity is basal GPCR activity. In certain embodiments, the cell or the cell population is not contacted with a GPCR ligand. Also described herein is a method for measuring the GPCR activity in a cell, the method comprising contacting the cell or the cell population with a GPCR ligand, where the ligand complexes with the GPCR and initiates or inhibits the GPCR activity. In certain embodiments, the GPCR ligand is expressed in the cell. In certain embodiments, the GPCR ligand is selected from the group consisting of a polypeptide, a non-peptide compound, and a small molecule.

BRIEF DESCRIPTION OF THE DRAWINGS

FIGS. 2A-2C illustrate gene expression cassette designs described herein to increase GPCR activity by changing the expression level of adenylyl cyclase (AC). FIG. 2A illustrates an exemplary second-generation gene expression cassette, where the AC3 expression can be knocked down, while the AC6 expression can be increased. FIG. 2B illustrates an exemplary third generation gene expression cassette, where the AC3 expression can be knocked down by targeting AC3 with multiple guide RNAs for downregulation of AC3 with a transcriptional repressor. FIG. 2C illustrates an exemplary first-generation gene expression cassette, where only the AC6 expression is increased.

DETAILED DESCRIPTION

Figure 1:
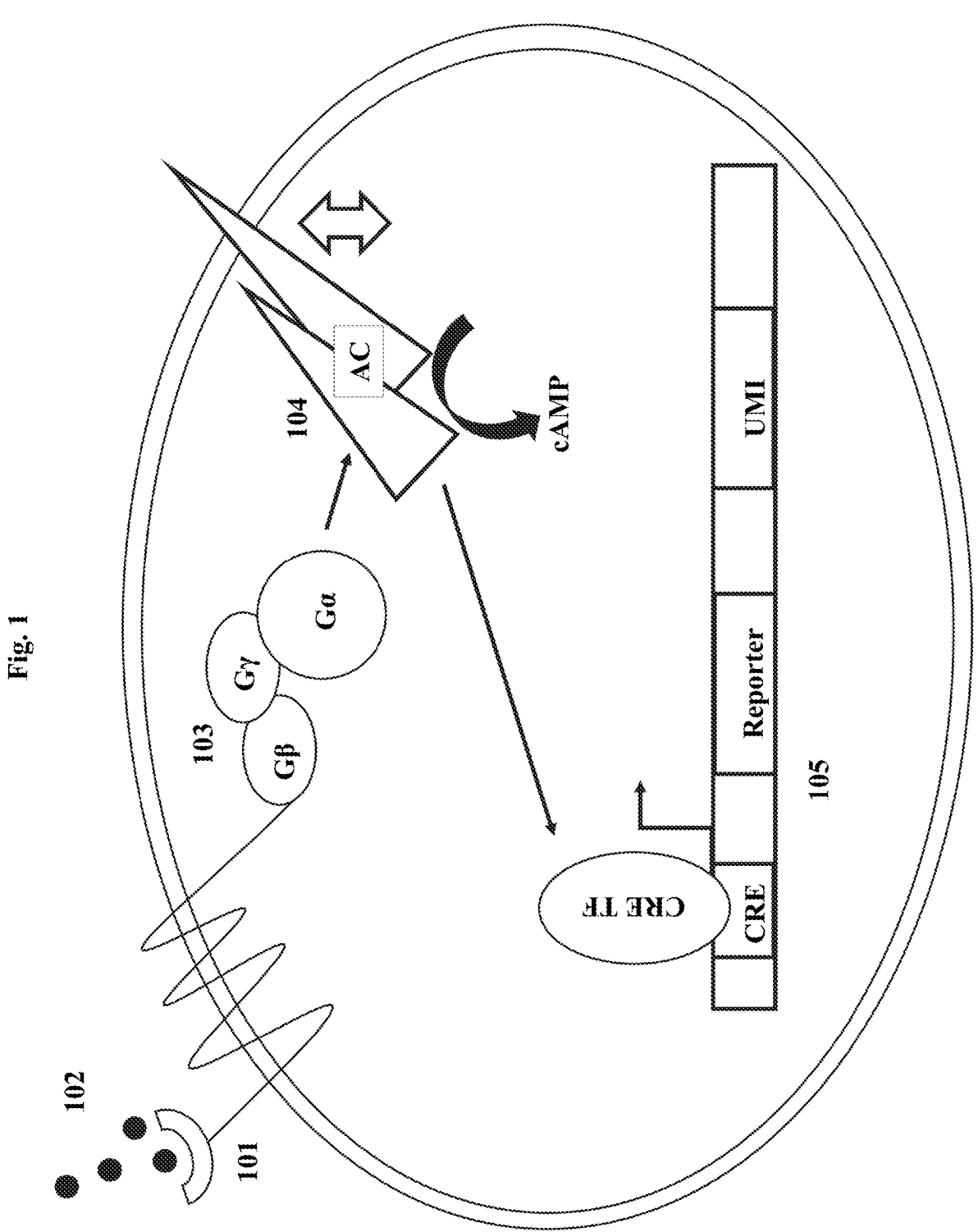
FIG. 1 illustrates an exemplary embodiment described herein, where the G protein-coupled receptor (GPCR) activity can be measured more accurately and robustly by upregulating or downregulating expressions of at least one family members of adenylyl cyclase (AC). The upregulation or downregulation of adenylyl cyclase is indicated by the double-headed arrow.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems and methods described herein are modular and not limited to sequential steps. Accordingly, terms such as "first" and "second" do not necessarily imply priority, order of importance, or order of acts.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. In some cases, "about" or "approximately refers to an amount that is near (plus or minus) the stated amount by 10%.

As used herein, the phrase "small molecule" refers to any molecule with low molecule weight (e.g., 900 Daltons). In some cases, the molecule can be organic compound that can regulate a biological process or reaction. In some cases, the small molecule can bind to a GPCR or a ligand of GPCR to increase or decrease GPCR activity. In some cases, the small molecule is a ligand for GPCR. Non-limiting examples of small molecule can include alfuzosin, terazosin, clonidine, bisoprolol, betaxolol, metoprolol, atenolol, albuterol, nadolol, penbutolol, tolterodine, atropine, scopolamine, calcimar, metoclopramide, haloperidol, olanzapine, ropinirole, pramipexole, loratadine, cetirizine, dimenhydrinate, cimetidine, ranitidine, trazodone, sumatriptan, exenatide, fentanyl, codeine, meperidine, oxycodone, montelukast, or misoprostol.

Where particular values are described in the application and claims, unless otherwise stated the term "about" should be assumed to mean an acceptable error range for the particular value.

The terms "increased", "increasing", or "increase" are used herein to generally mean an increase by a statically significant amount. In some cases, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased", "decreasing", or "decrease" are used herein generally to mean a decrease by a statistically significant amount. In some cases, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

As used herein, a "cell" generally refers to a biological cell. A cell is the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant, a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), or a cell from a mammal (e.g., a pig, a cow, a goat, a sheep, a rodent, a rat, a mouse, a non-human primate, a human, etc.). Sometimes a cell is not originating from a natural organism (e.g. a cell is a synthetically made, sometimes termed an artificial cell). In some cases, the cell is a primary cell. In some cases, the cell is derived from a cell line.

The term "nucleotide," as used herein, generally refers to a base-sugar-phosphate combination. A nucleotide comprises a synthetic nucleotide. A nucleotide comprises a synthetic nucleotide analog. Nucleotides is monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP.

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. In some cases, a polynucleotide is exogenous (e.g., a heterologous polynucleotide). In some cases, a polynucleotide is endogenous to a cell. In some cases, a polynucleotide can exist in a cell-free environment. In some cases, a polynucleotide is a gene or fragment thereof. In some cases, a polynucleotide is DNA. In some cases, a polynucleotide is RNA. A polynucleotide can have any three dimensional structure, and can perform any function, known or unknown. In some cases, a polynucleotide comprises one or more analogs (e.g., altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), guide RNA (gRNA), microRNA (miRNA), non-coding RNA, ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. In some cases, the sequence of nucleotides is interrupted by non-nucleotide components.

The terms "polypeptide" and "protein" are used interchangeably to refer to a polymer of amino acid residues, and are not limited to a minimum length. Polypeptides, including the provided polypeptide chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification. In some cases, the polypeptide encodes a gene or a transgene as described herein.

The term "gene" or "transgene" as used herein refers to a segment of nucleic acid that encodes an individual protein or RNA (also referred to as a "coding sequence" or "coding region"), optionally together with associated regulatory elements such as promoter, operator, terminator and the like, which is located upstream or downstream of the coding sequence. In some cases, the promoter is an inducible promoter. In some embodiments, the regulatory element comprises at least one open reading frame (ORF) that does not encode the transgene. Instead, the ORF in the regulatory element can upregulate the transgene. In some embodiments, the ORF in the regulatory element can downregulate the transgene. In some embodiments, the ORF in the regulatory element is located at a 5' upstream of the transgene. In some embodiments, the ORF in the regulatory element is located at a 3' downstream of the transgene. The term "gene" or "transgene" is to be interpreted broadly, and can encompass mRNA, cDNA, cRNA and genomic DNA forms of a gene. In some uses, the term "gene" encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" or "transgene" comprises only the coding sequences (e.g., an "open reading frame" or "coding region") necessary for encoding a polypeptide. In some aspects, genes or transgenes do not encode a polypeptide, for example, ribosomal RNA genes (rRNA) and transfer RNA (tRNA) genes. In some aspects, the term "gene" or "transgene" includes not only the transcribed sequences, but in addition, also includes non-transcribed regions including upstream and downstream regulatory elements such as regulatory regions, enhancers and promoters. The term "gene" or "transgene" can encompass mRNA, cDNA and genomic forms of a gene.

The term "inverse cyclic AMP activity refers to the reduction of cAMP activity or reduction of concentration of cAMP.

The term "expression" generally refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. In some embodiment, expression can include biological activity of the polypeptide encoded by the polynucleotide described herein. "Upregulate", with reference to expression, generally refers to an increased expression level of a polynucleotide (e.g., RNA such as mRNA) and/or polypeptide sequence compared to its expression level in a wild-type state. For example, an expression of gene or transgene can be upregulated by the systems described herein by at least 0.1 fold, 0.2 fold, 0.3 fold, 0.4 fold, 0.5 fold, 1 fold, 2 fold, 3 fold, 4 fold, 5 fold, 10 fold, 20 fold, 50 fold, or more fold compared to an expression of the gene or transgene in a wild-type state (e.g. without the systems described herein upregulating the expression of the gene or transgene). "Downregulate" generally refers to a decreased expression level of a polynucleotide (e.g., RNA such as mRNA) and/or polypeptide sequence compared to its expression in a wild-type state. For example, an expression of gene or transgene can be downregulated by the systems described herein by at least 0.1 fold, 0.2 fold, 0.3 fold, 0.4 fold, 0.5 fold, 1 fold, 2 fold, 3 fold, 4 fold, 5 fold, 10 fold, 20 fold, 50 fold, or more fold compared to an expression of the gene or transgene in a wild-type state (e.g., without the systems described herein upregulating the expression of the gene or transgene). "Wild-type" or "wild-type state" can refer to a phenotype or biological measurements or observations of the expression as it occurs in nature without manipulation by expression vectors or nucleic acids that reduce expression of a target (e.g., expression as a product of a normal allele as opposed to expression as a product of a mutant or engineered gene or by siRNA or a CRISPR/Cas9 system).

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared.

The terms "identity," "identical," or "percent identical" when used herein to describe to a nucleic acid sequence, compare to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent identity of sequences can be determined using the most recent version of BLAST, as of the filing date of this application.

The polypeptides of the systems described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In some cases, the vectors comprise regulatory elements such as promoters, enhancers, polyadenylation signals for use in controlling transcription. Regulatory elements can be derived from mammalian, microbial, viral or insect genes. In the embodiments, the vectors comprise the gene expression cassettes described herein. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements for integration.

As used herein the term "transfection" or "transfected" refers to methods that intentionally introduce an exogenous nucleic acid into a cell through a process commonly used in laboratories. Transfection can be effected by, for example, lipofection, calcium phosphate precipitation, viral transduction, or electroporation. Transfection can be either transient or stable.

As used herein the term "transfection efficiency" refers to the extent or degree to which a population of cells has incorporated an exogenous nucleic acid. Transfection efficiency can be measured as a percentage (%) of cells in a given population that have incorporated an exogenous nucleic acid compared to the total population of cells in a system. Transfection efficiency can be measured in both transiently and stably transfected cells.

As used herein, the term "biologically activating polypeptide" refers to a polypeptide expressed by a cell that modulates gene expression. The biologically activating polypeptide may modulate gene expression directly, through signaling via one or more intermediary molecules or polypeptides, in response to a stimuli, or through any other mechanism. A biologically activating polypeptide may be a transmembrane polypeptide (such as a receptor or a channel protein), an intracellular polypeptide (such as signal transduction intermediaries), an extracellular polypeptide, or a secreted polypeptide.

As used herein "reporter activity" refers to the empirical readout from the reporter. For example, a luciferase reporter will have a luminescent readout when incubated with an appropriate substrate. Other reporters like a fluorescent protein may not require a substrate but can be measured via microscopy or a fluorescence plate reader for example. In some embodiments, the reporter is encoded by a reporter nucleic acid. In some instances, the expression of the reporter is driven by a regulatory element or a promoter described herein. In some embodiment, the expression of the reporter is driven by a cAMP response element such as cAMP response element-binding protein (CREB).

Overview

The systems and methods described herein can measure GPCR activities by detecting the presence and/or level of activation of a response element binding promoter associated with the GPCR actives. Also described herein, are systems and methods for increasing GPCR activities. In some cases, the systems and methods described herein allow for GPCR activities with decreased background when measuring the GPCR activities compared to conventional reporter systems and methods for measuring GPCR activities. In some cases, the systems and methods described herein allow for GPCR activities with increased levels of cAMP signals compared to conventional reporter systems and methods for measuring GPCR activities. In some embodiments, the systems and methods described herein comprise at least one nucleic acid encoding an effector described herein. In some instances, the at least one nucleic acid comprises a regulatory element. In certain embodiments, a response element binding promoter is activated at the end of the GPCR activities (e.g. a signaling cascade of GPCR). In certain embodiments, the presence of a response element binding promoter can be measured before and after an external stimulus such as a peptide, a macromolecule, a compound, or a small molecule binding or complexing with the GPCR. In certain embodiments, the systems or methods are useful for screening for pharmaceutical discovery purposes. In some cases, the systems or methods minimally comprises at least one nucleic acid comprising a response element regulated promoter driving an expression of a reporter. In certain embodiments, the reporter is a polypeptide. In certain embodiments, the reporter can further comprise an unique molecular identifier (UMI) such as an unique nucleic acid sequence that be used to identify a specific cell type or a specific cell population.

By way of non-limiting example, the biologically activating polypeptide can comprise a particular G-coupled protein receptor (GPCR), of which there are several hundred known. Thus, the UMI element allows for easy and rapid interrogation of the signaling of several different biologically activating polypeptides in multiplex format. Additionally, the systems and methods provided herein decrease background through a response element regulated promoter. This allows for more accurate quantification and decreases the number of false positive test compounds in any multiplex screening for compounds that may activate a biologically activating polypeptide. In certain embodiments, the nucleic acid sequence encoding a reporter polypeptide is absent. In certain embodiments, the nucleic acid sequence encoding an UMI is absent. In certain embodiments, the nucleic acid sequence encoding an UMI is 5' of the nucleic acid sequence encoding the reporter polypeptide. In certain embodiments, the nucleic acid sequence encoding the reporter polypeptide is 5' of the nucleic acid sequence encoding an UMI.

In certain embodiments, a nucleic acid encoding a reporter encodes a reporter polypeptide. In certain embodiments, the reporter polypeptide is capable of being detected directly. In certain embodiments, the reporter polypeptide produces a detectable signal upon the protein's enzymatic activity to a substrate. In certain embodiments, detection of a reporter polypeptide can be accomplished quantitatively. In certain embodiments, the reporter polypeptide comprises a luciferase protein, a beta-galactosidase, a beta-glucuronidase, a chloramphenicol acetyltransferase, a secreted placental alkaline phosphatase, or combinations thereof. In certain embodiments, the reporter polypeptide is a luciferase protein, non-limiting examples of substrates include firefly luciferin, latia luciferin, bacterial luciferin, coelenterazine, dinoflagellate luciferin, vargulin, and 3-hydroxy hispidin.

In certain embodiments, a nucleic acid encoding a reporter can also encode an UMI. The UMI comprises a short sequence of nucleotides that is unique to the nucleic acid. The UMI can be 8, 9, 10, 11, 12, 13, 14, 15, 16, 17, 18, 19, 20, or more nucleotides in length. The UMI is capable of being detected in any suitable way that allows sequence determination of the UMI, such as by next-generation sequencing methods. Methods of detecting the UMI may be quantitative, and include next-generation sequencing methods.

In certain embodiments, described herein are methods of using the systems described herein comprising at least one nucleic acid encoding an effector described herein and a reporter nucleic acid for use in drug discovery. In certain embodiments, the method comprises contacting the nucleic acid(s) with a cell or population of cells under conditions sufficient for the nucleic acid(s) to be internalized and expressed by the cell (e.g., transfected); contacting the cell with a physical or chemical stimulus; and determining activation of the reporter by one or more assays. In certain embodiments, the method comprises contacting a cell or population of cells comprising nucleic acid(s) encoding a transcription factor nucleic acid and a reporter nucleic acid; and determining activation of the reporter by one or more assays.

One non-limiting embodiment of the present disclose is shown in FIG. 1. A cell 100 comprises the systems described herein for measuring the GPCR activities. The GPCR 101 is contacted with a GPCR ligand 102. Upon contacting between GPCR 101 and GPCR ligand 102, the Gα subunit of G protein 103 dissociates from the Gβ and Gγ to interact with various members of the adenylyl cyclase (AC) family 104. By upregulating or downregulating the expressions of various AC family members 104, the GPCR activities can be more robustly and accurately measured by detecting the presence and level of the expression of the reporter construct 105 described herein. In some cases, the reporter construct 105 can optionally comprise an unique molecular identifier (UMI) nucleic acid sequence that be used to identify a specific cell type or a specific cell population comprising the systems described herein.

GPCR Activity

Described herein, in some embodiments, are systems and methods for measuring GPCR activities in a cell. In some instances, the system comprises a first nucleic acid encoding a first effector of the GPCR activity. In some cases, the first nucleic acid can be operably coupled to a regulatory element configured to overexpress the first effector of the GPCR activities. In some embodiments, the regulatory element comprises a promoter, an enhancer, or a combination thereof. In some cases, the system can further comprise a second nucleic acid that decreases expression of a second effector of the GPCR activities. In some cases, the GPCR activities comprise activities caused by a ligand binding or complexing with the GPCR expressed by the cell. In some embodiments, the system comprises additional effectors The GPCR can be any GPCR that generates the GPCR activities. In some embodiments, the GPCR can be exogenous or endogenous to the cell comprising the systems described herein. For example, the GPCR can be an exogenous GPCR that is introduced as a transgene into the cell comprising the systems described herein. In some cases, the GPCR can be an endogenous GPCR to the cell harboring the systems described herein. In some cases, the GPCR can be stimulated by a ligand to generate the GPCR activities. In some embodiments, the GPCR can generate the GPCR activities independent or in the absence of a ligand complexing or binding to the GPCR. In some embodiments, the GPCR activities comprise orphan GPCR activities, where the GPCR activities can be generated from a putative ligand or an unknown ligand complexing or binding to the GPCR. Exemplary GPCR can include adenosine receptor, a β-adrenergic receptor, a neurotensin receptor, a muscarinic acid receptor, a 5-hydroxytryptamine receptor, a adrenoceptor, a anaphylatoxin receptor, a angiotensin receptor, a apelin receptor, a bombesin receptor, a bradykinin receptor, a cannabinoid receptor, a chemokine receptor, a cholecystokinin receptor, a dopamine receptor, a endothelin receptor, a free fatty acid receptor, a bile acid receptor, a galanin receptor, a motilin receptor, a ghrelin receptor, a glycoprotein hormone receptor, a GnRH receptor, a histamine receptor, a KiSS1-derived peptide receptor, a leukotriene and lipoxin receptor, a lysophospholipid receptor, a melanin-concentrating hormone receptor, a melanocortin receptor, a melatonin receptor, a neuromedin U receptor, a neuropeptide receptor, a N-formylpeptide family receptor, a nicotinic acid receptor, a opioid receptor, a opsin-like receptor, a orexin receptor, a P2Y receptor, a peptide P518 receptor, a platelet-activating factor receptor, a prokineticin receptor, a prolactin-releasing peptide receptor, a prostanoid receptor, a protease-activated receptor, a relaxin receptor, a somatostatin receptor, a SPC/LPC receptor, a tachykinin receptor, a trace amino receptor, a thyrotropin-releasing hormone receptor, a urotensin receptor, a vasopressin/oxytocin receptor, an orphan GPCR, a calcitonin receptor, a corticotropin releasing factor receptor, a glucagon receptor, a parathyroid receptor, a VIP/PACAP receptor, a LNB7TM receptor, a GABA receptor, a metabotropic glutamate receptor, or a calcium sensor receptor.

In some embodiments, the ligands complexing or binding to the GPCR described herein are known. In some cases, the ligand for the GPCR can be an agonist or a partial agonist and is able to complex or bind to the GPCR and increase the GPCR activities in the cell. In some embodiments, the ligand can be an inverse agonist, which the ligand binding or complexing to the GPCR reduces the basal GPCR activities. In some embodiments, the ligand complexing or binding to GPCR can be an antagonist, which binds to the GPCR and blocks binding of a GPCR agonist. In some cases, the ligand is a small organic or inorganic moiety. In some cases, the ligand can be a polypeptide. The polypeptide can be a naturally occurring GPCR-binding protein or other protein, derivative, or fragment thereof that can bind or complex with the GPCR. In some embodiments, the polypeptide can be an antibody that binds to the GPCR. Antibody can be any immunoglobulin, including any immunoglobulin isotypes, subclasses, monoclonal antibodies and fragments thereof comprising an antigen binding domains such as Fab, F(ab')2, single chain Fv (scFv), Fv, domain antibodies (dAbs), nanobodies and diabodies. In some embodiments, the ligand can be covalently connected with GPCR. In some embodiments, the ligand can be a peptidomimetic, a nucleic acid, a peptide nucleic acid (PNA), a macromolecule, or an aptamer. In some embodiments, the ligand can be an ion such as Na+ or Zn2+. In some embodiments, the ligand can be a lipid. In some embodiments, the ligand can be a carbohydrate. In some embodiments, the ligand can bind to the GPCR with a dissociation constant ($K_d$) from millimolar (mM) to picomolar (pM).

In some embodiments, the GPCR activities comprise G protein activities. In some cases, the G protein activity can be a stimulatory activity. In some instances, the G protein activity can be an inhibitory activity. The G protein activities can include activities of G protein alpha subunit (Gα), G protein beta subunit (Gβ), G protein gamma subunit (Gγ), and/or G protein beta and gamma subunits (Gβγ). In some cases, the G protein activities comprise activities of Gα. Gα activities can include activities of a $G_i$ alpha subunit, a $G_s$ alpha subunit activity, a $G_q$ alpha subunit activity, or a $G_{12}$ alpha subunit. In some cases, the G protein activity comprises $G_i$ alpha subunit activity. $G_i$ alpha subunit can include $G\alpha_{i1}$, $G\alpha_{i2}$, $G\alpha_{i3}$, $G\alpha_o$, $G\alpha_t$, $G\alpha_g$ or $G\alpha_z$. $G_5$ alpha subunit can include $G\alpha_s$ or $G\alpha_{olf}$. $G_q$ alpha subunit can include $G\alpha_q$, $G\alpha_{11}$, $G\alpha_{14}$, or $G\alpha_{16}$. $G_{12}$ alpha subunit can include $G\alpha_{12}$ or $G\alpha_{13}$. In some cases, Gβ subunit can include $G\beta_1$, $G\beta_2$, $G\beta_3$, $G\beta_4$, or $G\beta_5$. In some instances, Gγ subunit can include $G\gamma_1$, $G\gamma_2$, $G\gamma_3$, $G\gamma_4$, $G\gamma_5$, $G\gamma_6$, $G\gamma_7$, $G\gamma_8$, $G\gamma_9$, $G\gamma_{10}$, $G\gamma_{11}$, or $G\gamma_{12}$.

In some cases, the GPCR activities comprise activities of at least one effectors of GPCR. In some cases, the effector of GPCR includes a second messenger associated with the G protein. For example, GPCR activity includes activity effector such as adenylyl cycles, phospholipases, phosphodiesterases, kinases, or ion channels that are second messengers associated with the G protein activity. In some embodiments, the GPCR activity comprises cyclic AMP (cAMP) activity. In some embodiments, the GPCR activity comprises inverse cAMP activity. In some cases, the GPCR activity comprises downstream signaling of the messengers or molecules associated with the G protein. For example, the GPCR activity can comprise transcriptional or translational activity of a cAMP response element binding to the reporter nucleic acid described herein. In some cases, the GPCR activity can be measured from a detectable signal generated from the cAMP response element binding to the reporter nucleic acid described herein. In some embodiments, the GPCR activity is proportional to a detectable signal generated by the reporter described herein.

In some embodiments, the systems described herein comprise at least one nucleic acid to modulate expression of any one of the effectors described herein. In some cases, the nucleic acid encodes any one of the effectors described herein. In some embodiments, the nucleic acid encodes a regulatory element, which modulates the expression of the effector. In some embodiments, the regulatory element comprises a promoter, an enhancer, or a combination thereof. In some embodiments, the regulatory element comprises a promoter. In some embodiments, the regulatory element comprises an enhancer. In some embodiments, the regulatory element upregulates the expression of the effector. In some embodiments, the regulatory element downregulates the expression of the effector. In some embodiments, the nucleic acid encodes both the regulatory element and the effector, where the regulatory element upregulates the expression of the effector encoded by the nucleic acid. In some embodiments, the nucleic acid encodes both the regulatory element and the effector, where the regulatory element downregulates the expression of the effector encoded by the nucleic acid. In some embodiments, the at least one nucleic acid encodes any one of the effectors described herein and any one of the regulatory elements described herein. In some embodiments, the at least one nucleic acid encodes one effector and one regulatory element. For example, the at least one nucleic acid can encode an effector operatively coupled to a regulatory element. In some embodiments, the system described herein comprises at least a first effector comprising a first adenylyl cyclase and at least a second effector comprising a second adenylyl cyclase. In some embodiments, the first effector and the second effector are under expression control of different regulatory elements. In some embodiments, the first effector is encoded by a nucleic acid operatively coupled to a promoter or enhancer, where the promoter or the enhancer increases or overexpresses the expression of the first effector compared to a wild-type state. In some embodiments, the first adenylyl cyclase is encoded by a nucleic acid operatively coupled to a promoter or enhancer, where the promoter or the enhancer increases or overexpresses the expression of the first adenylyl cyclase compared to a wild-type state.

In some embodiments, In some embodiments, the effector modulated by the regulatory element is an adenylyl cyclase. In some embodiments, the adenylyl cyclase is ADCY1, ADCY2, ADCY3, ADCY4, ADCY5, ADCY6, ADCY7, ADCY8, ADCY9, or ADCY10. In some embodiments, the regulatory element upregulates any one of ADCY1, ADCY2, ADCY3, ADCY4, ADCY5, ADCY6, ADCY7, ADCY8, ADCY9, or ADCY10. In some embodiments, the regulatory element upregulates ADCY6. In some embodiments, the regulatory element downregulates any one of ADCY1, ADCY2, ADCY3, ADCY4, ADCY5, ADCY6, ADCY7, ADCY8, ADCY9, or ADCY10. In some embodiments, the nucleic acid encodes an RNA that can downregulate the expression of any one of the effectors described herein. In some embodiments, the RNA comprises short interfering RNA (siRNA), short-hairpin RNA (shRNA), guide RNA (gRNA), or microRNA (miRNA) to downregulate the expression of the effector. In some cases, the gRNA can recruit and for a complex with a gRNA-guided nuclease to direct the nuclease to digest the nucleic acid of the effector. Non-limiting examples of the gRNA-guided nuclease that can be recruited to digest the nucleic acid (and subsequently decreasing the expression) of the effector can include CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), and eukaryotic Argonaute (eAgo)); any derivative thereof; any variant thereof and any fragment thereof. In some embodiments, the gRNA-guided nuclease can be a CRISPR-associated (Cas) protein. In some embodiments, the gRNA-guided nuclease can be a CRISPR/Cas9 protein. In some embodiments, the gRNA-guided nuclease such as CRISPR/Cas9 protein can be encoded from the same nucleic acid that also encodes the gRNA. In some embodiments, the gRNA-guided nuclease such as CRISPR/Cas9 protein can be encoded from a different nucleic acid that encodes the gRNA, In some embodiments, the RNA comprises a microRNA to downregulate the expression of the effector. In some embodiments, the RNA comprising siRNA, shRNA, gRNA, or miRNA to downregulate any one of the adenylyl cyclase described herein (e.g. ADCY1, ADCY2, ADCY3, ADCY4, ADCY5, ADCY6, ADCY7, ADCY8, ADCY9, or ADCY10). In some embodiments, the RNA comprising siRNA, shRNA, miRNA, or gRNA to downregulate ADCY3.

In some embodiments, the at least one effector can be downregulated by knocking down or knocking out the activity of the at least one effector in a cell by contacting the cell with an inhibitor. In some cases, the inhibitor can be an inhibitor for GPCR. In some embodiments, the inhibitor can be an inhibitor for adenylyl cyclase. In some embodiments, the inhibitor can be an antagonist. In some embodiments, the antagonist can be an antagonist for GPCR. In some embodiments, the antagonist can be an antagonist for adenylyl cyclase. In some embodiments, the inhibitor can be an inverse agonist. In some embodiments, the antagonist can be an inverse agonist for GPCR. In some embodiments, the antagonist can be an inverse agonist for adenylyl cyclase. Exemplary inhibitors of adenylyl agonist can include KH7, MDL12330A, NKY80, SKF 83566, SQ22536, and ST034307.

In some embodiments, the system described herein comprises at least one effector upregulated by a first regulatory element and at least one other different effector downregulated by a second regulatory element. In some embodiments, the system comprises at least one adenylyl cyclase upregulated by a first regulatory element and at least one other different adenylyl cyclase downregulated by a second regulatory element. In some embodiments, the system comprises ADCY6 upregulated by a first regulatory element and ADCY3 downregulated by a second regulatory element.

In some embodiments, the at least one effector can be upregulated in a cell by contacting the cell with an activator. In some cases, the activator can be an activator for GPCR. In some embodiments, the activator can be an activator for adenylyl cyclase. In some embodiments, the activator can be an agonist. In some embodiments, the agonist can be an agonist for GPCR. In some embodiments, the agonist can be an agonist for adenylyl cyclase. Exemplary activator of adenylyl agonist can include Forskolin, NKH477, PACAP1-27, and PACAP1-38.

In some embodiments, the systems described herein increase GPCR activities. In some embodiments, the systems described herein increase measurable GPCR activities. In some embodiments, the measurable GPCR activity comprises measurable G protein activity. In some embodiments, the measurable GPCR activity comprises of G protein alpha subunit (G$\alpha$) activity, G protein beta subunit (G$\beta$) activity, G protein gamma subunit (G$\gamma$) activity, and/or G protein beta and gamma subunits (G$\beta\gamma$) activity. In some cases, the G protein comprises activity of G$\alpha$. G$\alpha$ activity can include activity of a G$_i$ alpha subunit, a G$_s$ alpha subunit activity, a G$_q$ alpha subunit activity, or a G$_{12}$ alpha subunit. In some cases, the G protein activity comprises G$_i$ alpha subunit activity. In some embodiments, the system increases G$_i$ alpha subunit activity in a cell comprising the system compared to G$_i$ alpha subunit activity in a cell without the system. In some embodiments, the system increases measurable Gi alpha subunit activity in a cell by at least about 0.1 fold to about 10,000 fold. In some embodiments, the system increases measurable Gi alpha subunit activity in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system increases measurable Gi alpha subunit activity in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system increases measurable Gi alpha subunit activity in a cell by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system increases measurable Gi alpha subunit activity in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, GPCR activity comprises measurable cAMP activity. In some cases, measurable cAMP activity comprises an increase or decrease in cAMP concentration. In some embodiments, the system increases measurable cAMP activity in a cell comprising the system compared to cAMP activity in a cell without the system. In some embodiments, the system increases measurable cAMP in a cell by at least about 0.1 fold to about 10,000 fold. In some embodiments, the system increases cAMP in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system increases cAMP in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system increases cAMP in a cell by at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system increases cAMP in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, GPCR activity comprises measurable inverse cAMP activity. In some embodiments, the system increases measurable inverse cAMP activity in a cell comprising the system compared to inverse cAMP activity in a cell without the system. In some embodiments, the system increases inverse cAMP in a cell by at least about 0.1 fold to about 10,000 fold. In some embodiments, the system increases inverse cAMP by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system increases inverse cAMP by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system increases inverse cAMP by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system increases inverse cAMP by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, the system increases a measurable ratio between GPCR activity and background during measurements of the GPCR activity in a cell comprising the system compared to a measurable ratio between GPCR activity and background in a cell without the system. In some embodiments, the system increases a measurable ratio between GPCR activity and background in a cell by at least about 0.1 fold to about 10,000 fold. In some embodiments, the system increases a measurable ratio between GPCR activity and background in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system increases a ratio between GPCR activity and background in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system increases a ratio between GPCR activity and background in a cell by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system increases a ratio between GPCR activity and background in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, the system decreases background during measurements of GPCR activity in a cell comprising the system compared to background in a cell without the system. In some embodiments, background in a cell comprising the system, during measurements of GPCR activities, is decreased by at least about 0.1 fold to about 10,000 fold. In some embodiments, background in a cell comprising the system, during measurements of GPCR activities, is decreased by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, background in a cell comprising the system, during measurements of GPCR activities, is decreased by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, background in a cell comprising the system, during measurements of GPCR activities, is decreased by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, background in a cell comprising the system, during measurements of GPCR activities, is decreased by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, the system decreases measurable coefficient of variation of GPCR activity measurements in a cell comprising the system compared to measurable coefficient of variation of GPCR activity measurements in a cell without the system. In some embodiments, the system decreases measurable coefficient of variation of GPCR activity measurements in a cell by at least about 0.1 fold to about 10,000 fold. In some embodiments, the system decreases measurable coefficient of variation of GPCR activity measurements in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system decreases coefficient of variation of GPCR activity measurements in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system decreases coefficient of variation of GPCR activity measurements in a cell by at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system decreases coefficient of variation of GPCR activity measurements in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, the system decreases measurable false positive of GPCR activity measurements in a cell comprising the system compared to measurable false positive of GPCR activity measurements in a cell without the system. In some embodiments, the system decreases measurable false positive of GPCR activity measurements in a cell by at least about 0.1 fold to about 10,000 fold. In some embodiments, the system decreases measurable false positive of GPCR activity measurements in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system decreases false positive of GPCR activity measurements in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system decreases false positive of GPCR activity measurements in a cell by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system decreases false positive of GPCR activity measurements in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

In some embodiments, the system decreases measurable false negative of GPCR activity measurements in a cell comprising the system compared to measurable false negative of GPCR activity measurements in a cell without the system. In some embodiments, the system decreases measurable false negative of GPCR activity measurements in a cell by at least about 0.1 fold to about 10,000 fold. In some embodiments, the system decreases measurable false negative of GPCR activity measurements in a cell by at least about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.1 fold to about 500 fold, about 0.1 fold to about 1,000 fold, about 0.1 fold to about 10,000 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 0.5 fold to about 500 fold, about 0.5 fold to about 1,000 fold, about 0.5 fold to about 10,000 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 1 fold to about 500 fold, about 1 fold to about 1,000 fold, about 1 fold to about 10,000 fold, about 2 fold to about 5 fold, about 2 fold to about 10 fold, about 2 fold to about 20 fold, about 2 fold to about 50 fold, about 2 fold to about 100 fold, about 2 fold to about 500 fold, about 2 fold to about 1,000 fold, about 2 fold to about 10,000 fold, about 5 fold to about 10 fold, about 5 fold to about 20 fold, about 5 fold to about 50 fold, about 5 fold to about 100 fold, about 5 fold to about 500 fold, about 5 fold to about 1,000 fold, about 5 fold to about 10,000 fold, about 10 fold to about 20 fold, about 10 fold to about 50 fold, about 10 fold to about 100 fold, about 10 fold to about 500 fold, about 10 fold to about 1,000 fold, about 10 fold to about 10,000 fold, about 20 fold to about 50 fold, about 20 fold to about 100 fold, about 20 fold to about 500 fold, about 20 fold to about 1,000 fold, about 20 fold to about 10,000 fold, about 50 fold to about 100 fold, about 50 fold to about 500 fold, about 50 fold to about 1,000 fold, about 50 fold to about 10,000 fold, about 100 fold to about 500 fold, about 100 fold to about 1,000 fold, about 100 fold to about 10,000 fold, about 500 fold to about 1,000 fold, about 500 fold to about 10,000 fold, or about 1,000 fold to about 10,000 fold. In some embodiments, the system decreases false negative of GPCR activity measurements in a cell by at least about 0.1 fold, about 0.5 fold, about 1 fold, about 2 fold, about 5 fold, about 10 fold, about 20 fold, about 50 fold, about 100 fold, about 500 fold, about 1,000 fold, or about 10,000 fold. In some embodiments, the system decreases false negative of GPCR activity measurements in a cell by at least at least about 0.1 fold, about 0.5 fold, about 1 fold, about 2 fold, about 5 fold, about 10 fold, about 20 fold, about 50 fold, about 100 fold, about 500 fold, or about 1,000 fold. In some embodiments, the system decreases false negative of GPCR activity measurements in a cell by at least at most about 0.5 fold, about 1 fold, about 2 fold, about 5 fold, about 10 fold, about 20 fold, about 50 fold, about 100 fold, about 500 fold, about 1,000 fold, or about 10,000 fold.

Response Element Regulated Promoters

Response elements are short sequences of DNA within a gene promoter region that are able to be bound by specific transcription factors and regulate transcription of genes. Certain response elements are specific to certain promoters. Some response elements are capable of being bound by endogenous transcription factors. Multiple copies of the same response element can be located in different portions of a nucleotide sequence, activating different genes in response to the same stimuli. Non-limiting examples of response elements that can be incorporated in to the system described herein include cAMP response element (CRE), B recognition element, AhR-, dioxin- or xenobiotic-responsive element, HIF-responsive elements, hormone response elements, serum response element, retinoic acid response elements, peroxisome proliferator hormone response elements, metal-responsive element, DNA damage response element, IFN-stimulated response elements, ROR-response element, glucocorticoid response element, calcium-response element CaRE1, antioxidant response element, p53 response element, thyroid hormone response element, growth hormone response element, sterol response element, polycomb response elements, and vitamin D response element.

Response element regulated promoter nucleotide sequences are regions of nucleic acids containing one or more response elements that aid in recruiting promoters and other molecules to regulate transcription of genes. Cells contain many response element regulated nucleotide sequences that utilize endogenous proteins to modulate transcription of genes. In situations where an endogenous response element regulated promoter nucleotide sequence directly regulates transcription of a reporter, there exists a high level of background signal due to the presence of endogenous promoters. A system that regulates transcription of a reporter with a transcription factor that is not endogenous to a cell containing the system would have advantages over a system that regulates transcription of a reporter with an endogenous transcription factor. One advantage of such a system would be a lower background production of the reporter.

Reporter

The reporter nucleic acid minimally comprises a regulatory element that is able to be bound by a transcription factor (e.g. a cAMP response element (CRE) binding protein) associated with the GPCR activities and a nucleotide sequence encoding a reporter. The nucleotide sequence encoding a reporter is downstream of the regulatory element that is able to be bound by the transcription factor associated with the GPCR activities. The transcription associated with the GPCR activities regulates expression of the reporter.

In certain embodiments, the nucleotide sequence encoding a reporter comprises a reporter gene. In certain embodiments, the reporter gene encodes a reporter selected from a fluorescent protein, a luciferase protein, a beta-galactosidase, a beta-glucuronidase, a chloramphenicol acetyltransferase, and a secreted placental alkaline phosphatase. These reporter proteins can be assayed for a specific enzymatic activity or in the case of a fluorescent reporter can be assayed for fluorescent emissions. In certain embodiments, the fluorescent protein comprises a green fluorescent protein (GFP), a red fluorescent protein (RFP), a yellow fluorescent protein (YFP), or a cyan fluorescent protein (CFP).

In certain embodiments, the nucleotide sequence encoding a reporter gene comprises a nucleotide sequence encoding a unique sequence identifier (UMI). In certain embodiments, the UMI is unique to a test polypeptide, where the test polypeptide is encoded by the reporter nucleic acid. Generally, the UMI will be between 8 and 20 nucleotides in length, however it may be longer. In certain embodiments, the UMI is 8, 9, 10, 11, 12, 13, 14, 15, 16, 17, 18, 19, 20, or more nucleotides in length. In certain embodiments, the UMI is 8 nucleotides in length. In certain embodiments, the UMI is 9 nucleotides in length. In certain embodiments, the UMI is 10 nucleotides in length. In certain embodiments, the UMI is 11 nucleotides in length. In certain embodiments, the UMI is 12 nucleotides in length. In certain embodiments, the UMI is 13 nucleotides in length. In certain embodiments, the UMI is 14 nucleotides in length. In certain embodiments, the UMI is 15 nucleotides in length. In certain embodiments, the UMI is 16 nucleotides in length. In certain embodiments, the UMI is 17 nucleotides in length. In certain embodiments, the UMI is 18 nucleotides in length. In certain embodiments, the UMI is 19 nucleotides in length. In certain embodiments, the UMI is 20 nucleotides in length. In certain embodiments, the UMI is more than 20 nucleotides in length.

The system described herein can utilize many different regulatory sequences that control activation of the reporter gene through the binding of transcription factor (e.g. CREB) associated with the GPCR activities. The regulatory sequence is one that can be bound by the transcription factor associated with the GPCR activities. Generally, it will be configured so that the regulatory sequence is 5' to the UMI, the reporter gene, or both. In certain embodiments, the regulatory sequence comprises a Gal4-, PPR1-, or LexA-UAS, which is able to be bound by the transcription factor associated with the GPCR activities.

In certain embodiments, the reporter comprises a fluorescent protein, a luciferase protein, a beta-galactosidase, a beta-glucuronidase, a chloramphenicol acetyltransferase, or a secreted placental alkaline phosphatase, and an UMI. In certain embodiments, the UMI is encoded on the reporter nucleic acid 5' of the fluorescent protein, luciferase protein, beta-galactosidase, beta-glucuronidase, chloramphenicol acetyl transferase, or secreted placental alkaline phosphatase. In certain embodiments, a nucleotide sequence encoding the fluorescent protein, luciferase protein, beta-galactosidase, beta-glucuronidase, chloramphenicol acetyl-transferase, or secreted placental alkaline phosphatase is 5' of the UMI.

An UMI allows for multiplexing of different systems within the same assay since transcription of the UMI will indicate association of a specific system with the reporter. The UMI can be any length that allows for sufficient diversity to allow multiplexed determination of different systems within the same assay. The length should be sufficient to differentiate between at least 100, 500, 1,000, 2,000, 3,000, 4,000, 5,000, 6,000, 7,000, 8,000, 9,000, or 10,000 targets. In certain embodiments, the different systems will be present in different cells. In certain embodiments, the different systems will be present in the same cell. Reporter elements may further comprise a 5' UTR, a 3'UTR or both. The UTR may be heterologous to the reporter element.

Reporter Activation

Activation of a reporter molecule can be determined using standard assays to detect a luciferase protein, a beta-galactosidase protein, a beta-glucuronidase protein, a chloramphenicol acetyltransferase protein, a secreted placental alkaline phosphatase protein. Generally, these are enzymatic assays where a detectable signal is produced based upon the proteins enzymatic activity towards a substrate. For example, luciferase expression can be measured in the presence of a luciferase substrate by a luminometer. A fluorescent reporter does not require a substrate, and the signal can be measured by fluorescence microscopy or a fluorescent plate reader. Fluorescent reporters are particularly useful for measuring reporter activation in live cells.

In some embodiments, a reporter molecule comprises an unique RNA sequence, such as a unique molecular identifier (UMI), also referred to as an index sequence or a barcode sequence. Reporter activation can be measured in any suitable way that allows sequence determination of the unique RNA sequence, with a preference for methods that allow sequence determination in a multiplex fashion. Such methods include high throughput sequencing methods that can generate information on at least about 100,000, 1,000,000, 10,000,000, or 100,000,000 DNA or RNA bases in a 24-hour period. In certain embodiments, a next-generation sequencing technology is used to determine the sequence of the unique RNA sequence. Next generation sequencing encompasses many kinds of sequencing such as pyrosequencing, sequencing-by-synthesis, single-molecule sequencing, second-generation sequencing, nanopore sequencing, sequencing by ligation, or sequencing by hybridization. Next-generation sequencing platforms include those commercially available from Illumina (RNA-Seq) and Helicos (Digital Gene Expression or "DGE"). Next generation sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos Biosciences Corporation (Cambridge, MA) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina, Inc. as described in U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. Such methods and apparatuses are provided here by way of example and are not intended to be limiting.

Cells

Cells useful for the systems and methods described herein are generally those that are able to be easily rendered transgenic with one or more nucleic acids described herein. The system nucleic acid(s) encoding a regulatory element, an effector, and/or a reporter element can be transfected or transduced into suitable cell line using methods known in the art, such as calcium phosphate transfection, lipid based transfection (e.g., Lipofectamine™, Lipofectamine-2000™, Lipofectamine-3000™, or Eugene® HD), electroporation, or viral transduction. The cell can also be a population of cells of the same type grown to confluency or near confluency in an appropriate tissue culture vessel.

In certain embodiments, the cell used herein comprises a stable integration of either the nucleic acid encoding the regulatory element, the nucleic acid encoding the effector, the nucleic acid comprising the reporter element, or a combination thereof. Stable cell lines can be made from the cell described herein by using random integration of a linearized plasmid, virally or transposon directed integration, or directed integration, for example using site specific recombination between an AttP and an AttB site. In certain embodiments, either of the nucleic acids are integrated at a safe landing site such as the AAVS1 site.

In some embodiments, the cell described herein comprises the nucleic acid stably integrated into the genome of the cell. In some embodiments, the cell described herein comprises the nucleic acid encoding the regulatory element stably integrated into the genome of the cell. In some embodiments, the cell described herein comprises the nucleic acid encoding at least one effector described herein stably integrated into the genome of the cell. In some cases, the effector is a GPCR effector. In some cases, the GPCR effector is an adenylyl cyclase selected from the group:

ADCY1, ADCY2, ADCY3, ADCY4, ADCY5, ADCY6, ADCY7, ADCY8, ADCY9, or ADCY10. In some embodiments, the cell comprises stably integrated nucleic acid encoding a regulatory element for modulating expression of the effector. In some cases, the cell comprises stably integrated nucleic acid encoding a regulatory element for upregulating the effector described herein. In some cases, the cell comprises stably integrated nucleic acid encoding a regulatory element for upregulating ADCY6. In some cases, the cell comprises stably integrated nucleic acid encoding ADCY6. In some cases, the cell comprises stably integrated nucleic acid encoding a regulatory element for downregulating the effector described herein. In some cases, the cell comprises stably integrated nucleic acid encoding a regulatory element for downregulating ADCY3.

In certain embodiments, the cell or cell population used in the system is a eukaryotic cell. In certain embodiments, the cell or cell population is a mammalian cell. In certain embodiments, the cell or cell population is a human cell. In certain embodiments, the cell or cell population is SH-SY5Y, Human neuroblastoma; Hep G2, Human Caucasian hepatocyte carcinoma; 293 (also known as HEK 293), Human Embryo Kidney; RAW 264.7, Mouse monocyte macrophage; HeLa, Human cervix epithelioid carcinoma; MRC-5 (PD 19), Human fetal lung; A2780, Human ovarian carcinoma; CACO-2, Human Caucasian colon adenocarcinoma; THP 1, Human monocytic leukemia; A549, Human Caucasian lung carcinoma; MRC-5 (PD 30), Human fetal lung; MCF7, Human Caucasian breast adenocarcinoma; SNL 76/7, Mouse SIM strain embryonic fibroblast; C2C12, Mouse C3H muscle myoblast; Jurkat E6.1, Human leukemic T cell lymphoblast; U937, Human Caucasian histiocytic lymphoma; L929, Mouse C3H/An connective tissue; 3T3 L1, Mouse Embryo; HL60, Human Caucasian promyelocytic leukaemia; PC-12, Rat adrenal phaeochromocytoma; HT29, Human Caucasian colon adenocarcinoma; OE33, Human Caucasian oesophageal carcinoma; OE19, Human Caucasian oesophageal carcinoma; NIH 3T3, Mouse Swiss NIH embryo; MDA-MB-231, Human Caucasian breast adenocarcinoma; K562, Human Caucasian chronic myelogenous leukemia; U-87 MG, Human glioblastoma astrocytoma; MRC-5 (PD 25), Human fetal lung; A2780cis, Human ovarian carcinoma; B9, Mouse B cell hybridoma; CHO-K1, U205, Hamster Chinese ovary; MDCK, Canine Cocker Spaniel kidney; 1321N1, Human brain astrocytoma; A431, Human squamous carcinoma; ATDC5, Mouse 129 teratocarcinoma AT805 derived; RCC4 PLUS VECTOR ALONE, Renal cell carcinoma cell line RCC4 stably transfected with an empty expression vector, pcDNA3, conferring neomycin resistance; HUVEC (5200-05n), Human Pre-screened Umbilical Vein Endothelial Cells (HUVEC); neonatal; Vero, Monkey African Green kidney; RCC4 PLUS VHL, Renal cell carcinoma cell line RCC4 stably transfected with pcDNA3-VHL; Fao, Rat hepatoma; J774A.1, Mouse BALB/c monocyte macrophage; MC3T3-E1, Mouse C57BL/6 calvaria; J774.2, Mouse BALB/c monocyte macrophage; PNT1A, Human post pubertal prostate normal, immortalised with SV40; U-2 OS, Human Osteosarcoma; HCT 116, Human colon carcinoma; MA104, Monkey African Green kidney; BEAS-2B, Human bronchial epithelium, normal; NB2-11, Rat lymphoma; BHK 21 (clone 13), Hamster Syrian kidney; NS0, Mouse myeloma; Neuro 2a, Mouse Albino neuroblastoma; SP2/0-Ag14, Mouse×Mouse myeloma, non-producing; T47D, Human breast tumor; 1301, Human T-cell leukemia; MDCK-II, Canine Cocker Spaniel Kidney; PNT2, Human prostate normal, immortalized with SV40; PC-3, Human Caucasian prostate adenocarcinoma; TF1, Human erythroleukaemia; COS-7, Monkey African green kidney, SV40 transformed; MDCK, Canine Cocker Spaniel kidney; HUVEC (200-05n), Human Umbilical Vein Endothelial Cells (HUVEC); neonatal; NCI-H322, Human Caucasian bronchioalveolar carcinoma; SK.N.SH, Human Caucasian neuroblastoma; LNCaP.FGC, Human Caucasian prostate carcinoma; OE21, Human Caucasian oesophageal squamous cell carcinoma; PSN1, Human pancreatic adenocarcinoma; ISHIKAWA, Human Asian endometrial adenocarcinoma; MFE-280, Human Caucasian endometrial adenocarcinoma; MG-63, Human osteosarcoma; RK 13, Rabbit kidney, BVDV negative; EoL-1 cell, Human eosinophilic leukemia; VCaP, Human Prostate Cancer Metastasis; tsA201, Human embryonal kidney, SV40 transformed; CHO, Hamster Chinese ovary; HT 1080, Human fibrosarcoma; PANC-1, Human Caucasian pancreas; Saos-2, Human primary osteogenic sarcoma; Fibroblast Growth Medium (116K-500), Fibroblast Growth Medium Kit; ND7/23, Mouse neuroblastoma×Rat neuron hybrid; SK-OV-3, Human Caucasian ovary adenocarcinoma; COV434, Human ovarian granulosa tumor; Hep 3B, Human hepatocyte carcinoma; Vero (WHO), Monkey African Green kidney; Nthy-ori 3-1, Human thyroid follicular epithelial; U373 MG (Uppsala), Human glioblastoma astrocytoma; A375, Human malignant melanoma; AGS, Human Caucasian gastric adenocarcinoma; CAKI 2, Human Caucasian kidney carcinoma; COLO 205, Human Caucasian colon adenocarcinoma; COR-L23, Human Caucasian lung large cell carcinoma; IMR 32, Human Caucasian neuroblastoma; QT 35, Quail Japanese fibrosarcoma; WI 38, Human Caucasian fetal lung; HMVII, Human vaginal malignant melanoma; HT55, Human colon carcinoma; TK6, Human lymphoblast, thymidine kinase heterozygote; SP2/0-AG14 (AC-FREE), Mouse×mouse hybridoma non-secreting, serum-free, animal component (AC) free; AR42J, or Rat exocrine pancreatic tumor, or any combination thereof.

In certain embodiments, the cell or cell line comprises a high basal reporter activity. In certain embodiments, the high basal reporter activity is at least about 5%, 10%, 20%, 25%, 30%, 40%, 50%, 60%, 70%, 80%, 90%, 100%, 200%, 300%, 400%, 500% greater than background, where the background is the level of reporter activity observed for a cell or cell line that does not comprise the reporter. In certain embodiments, the high basal reporter activity is at least about 5%, 10%, 20%, 25%, 30%, 40%, 50%, 60%, 70%, 80%, 90%, 100%, 200%, 300%, 400%, 500% greater than background, where the background is the level of reporter activity observed for a cell or cell line that does not comprise the system described herein. For such comparisons, generally the cell or cell line used as a comparator will be parental to the cell line comprising the system (e.g., HEK293 with system vs. HEK293 without system).

In certain embodiments, the cell or cell line comprises a high basal reporter activity. In certain embodiments, the high basal reporter activity is at least about 2×, 3×, 4×, 5×, 6×, 7×, 8×, 9×, 10×, 15×, 20×, 25×, 30×, 32×, 50×, 75×, 100×, 200×, 500×, 750×, 1,000×, 2,000×, 5,000×10,000×, or 20,000× greater than background, where the background is the level of reporter activity observed for a cell or cell line that does not comprise the reporter. In certain embodiments, the high basal reporter activity is at least about 2×, 3×, 4×, 5×, 6×, 7×, 8×, 9×, 10×, 15×, 20×, 25×, 30×, 32×, 50×, 75×, 100×, 200×, 500×, 750×, 1,000×, 2,000×, 5,000×10,000×, or 20,000× greater than background, where the background is the level of reporter activity observed for a cell or cell line that does not comprise the system described herein. In certain embodiments, the cell or cell line comprises a high basal reporter activity. In certain embodiments, the high basal reporter activity is at least about 30× greater than background, where the background is the level of reporter activity observed for a cell or cell line that does not comprise the reporter. In certain embodiments, the high basal reporter activity is at least about 30× greater than background, where the background is the level of reporter activity observed for a cell or cell line that does not comprise the system described herein. For such comparisons, generally the cell or cell line used as a comparator will be parental to the cell line comprising the system (e.g., HEK293 with system vs. HEK293 without system).

In certain embodiments, the cell or cell line comprises low variance in basal reporter activity. In certain embodiments, the low variance in basal reporter activity is a biological coefficient of variance less than about 0.6. In certain embodiments, the low variance in basal reporter activity is a biological coefficient of variance less than about 0.5. In certain embodiments, the low variance in basal reporter activity is a biological coefficient of variance less than about 0.4. In certain embodiments, the low variance in basal reporter activity is a biological coefficient of variance less than about 0.3. In certain embodiments, the low variance in basal reporter activity is a biological coefficient of variance less than about 0.2. In certain embodiments, the low variance in basal reporter activity is a biological coefficient of variance less than about 0.1

Methods for Measuring GPCR Activities

The systems described herein can be effectively utilized using a variety of methods for measuring GPCR activities. The system is useful in methods to measure GPCR activities of cell signaling pathways, both at a steady-state and in response to a physical or chemical stimulus. When the reporter element comprises an UMI sequence mated to a particular reporter element, the system can be deployed in a multiplexed assay.

In one non-limiting, illustrative example, a plurality of cells are incubated in one well of a multi-well plate. The plurality of cells are transfected with at least one of the nucleic acid described herein. In some embodiments, the nucleic acid encodes a regulatory element described herein. In some embodiments, the nucleic acid encodes an effector described herein. In some embodiments, the nucleic acid encodes a reporter described herein. The transfected cells are then contacted with a ligand for a GPCR. After a sufficient amount of time to allow for expression of the reporter, cell lysates can be harvested, and activation of the reporter gene measured. In this example, increased presence of a reporter gene would be indicative of a ligand binding or complexing to the GPCR to cause an increase in the GPCR activity. In some cases, the increased presence of a reporter gene would be indicative of a ligand binding or complexing to the GPCR to cause an increase in the GPCR activity comprising $G_i$ alpha subunit activity. In some cases, the increased presence of a reporter gene would be indicative of a ligand binding or complexing to the GPCR to cause an increase in the GPCR activity comprising cAMP activity. In some cases, the increased presence of a reporter gene would be indicative of a ligand binding or complexing to the GPCR to cause an increase in the GPCR activity comprising inverse cAMP activity. In some embodiments, the transfected cell contacted with the ligand exhibits increased GPCR activity compared to the GPCR activity of a cell not transfected with the system described herein. In some embodiments, the transfected cell contacted with the ligand exhibits increased $G_i$ alpha subunit activity compared to the GPCR activity of a cell not transfected with the system described herein. In some embodiments, the transfected cell contacted with the ligand exhibits increased cAMP activity compared to the GPCR activity of a cell not transfected with the system described herein. In some embodiments, the transfected cell contacted with the ligand exhibits increased inverse cAMP activity compared to the GPCR activity of a cell not transfected with the system described herein.

In some embodiments, the reporter gene comprises an enzyme that produces a detectable signal upon interaction with a substrate, standard assays known in the art can be utilized to quantify activation the reporter gene. In some embodiments, the reporter gene comprises a fluorescent molecule, the activation of the reporter gene can be measured by fluorescence microscopy or a fluorescent plate reader, and may not require cell lysis. The fluorescent molecules are useful for measuring reporter activation in live cells. In some embodiments, the reporter gene comprises UMI, mRNA is reverse transcribed, and sequencing of the UMI is performed by next-generation sequencing technology.

In certain embodiments, the assays are carried out in multiwell formats such as 6, 12, 24, 48, 96, or 384-well format. In certain embodiments, each well is supplied with a different test chemical (e.g., ligand), or the test chemicals are supplied in duplicate, triplicate, or quadruplicate wells. The assay can also comprise one or more positive or a negative control wells. In some embodiments, the method comprises measuring GPCR activities in cell populations transfected with the at least one nucleic acid described herein. Cell populations transfected with the at least one nucleic acid of the present disclosure can be any size. In certain embodiments, cell populations comprise 1,000, 10,000, 100,000, 1,000,000, 10,000,000 or more cells. In certain embodiments, at least about 1,000 or more cells are transfected with the at least one nucleic acid of the system described herein. In certain embodiments, at least about 10,000 or more cells are transfected with the at least one nucleic acid of the system described herein. In certain embodiments, at least about 100,000 or more cells are transfected with the at least one nucleic acid of the system described herein. In certain embodiments, at least about 1,000,000 or more cells are transfected with the at least one nucleic acid of the system described herein. In certain embodiments, at least about 10,000,000 or more cells are transfected with the at least one nucleic acid of the system described herein. In certain embodiments, the systems of the present disclosure can be utilized in multiwell plate experiments. Non-limiting examples of multiwell plates compatible with the systems of the present disclosure include 6, 12, 24, 48, 96, 384, or 1,536 well plates. In certain embodiments, each well of a multiwell plate comprises a cell population transfected with the at least one nucleic acid of the system described herein. In certain embodiments, each well of a multiwell plate comprises a cell population transfected with the at least one nucleic acid of the system described herein. In certain embodiments, each well comprises multiple cell populations, each cell population transfected with the at least one nucleic acid of the system described herein. In certain embodiments, each well comprises multiple cell populations, each cell population transfected with the at least one nucleic acid of the system described herein.

One strength of the current systems is that libraries of cells expressing different targets can be cultured together in the same well and analyzed in parallel, for example allowing 2, 3, 4, 5, 6, 7, 8, 9, 10, 20, 30, 40, 50, 100, 200, 500, 1,000 or more targets in the same experiment. This is achieved by the targets being associated with a UMI unique for that target, the UMIs can then be analyzed by high-throughput sequencing deconvolving the data. Thus, in certain embodiments, described herein is a system comprising: a plurality of mammalian cells, wherein each of the plurality of mammalian cells comprise a different GPCR target and each cell of the plurality of mammalian cells comprises: a) a first effector of GPCR activity, wherein an expression of the first effector of GPCR activity is upregulated compared to an expression of the first effector of GPCR activity in a wild-type state; and b) a second effector of GPCR activity, wherein an expression of the second effector of GPCR activity is downregulated compared to an expression of the second effector of GPCR activity in a wild-type state. In certain embodiments, the plurality of mammalian cells further comprise a reporter gene comprising a unique molecular identifier (UMI) nucleic acid sequence, the reporter gene able4 to be activated by a promoter responsive to GPCR signaling.

Thus, in certain embodiments, described herein is a system comprising: a plurality of mammalian cells, wherein each of the plurality of mammalian cells comprise a different target and each cell of the plurality of mammalian cells comprises: a) a first effector of target activity, wherein an expression of the first effector of target activity is upregulated compared to an expression of the first effector of target activity in a wild-type state; and b) a second effector of target activity, wherein an expression of the second effector of target activity is downregulated compared to an expression of the second effector of target activity in a wild-type state. In certain embodiments, the plurality of mammalian cells further comprise a reporter gene comprising a unique molecular identifier (UMI) nucleic acid sequence, the reporter gene able4 to be activated by a promoter responsive to target signaling.

In certain embodiments, test agents such as ligands complexing or binding to the GPCR are applied to cells transfected with the at least one nucleic acid of the system described herein. In certain embodiments, level of activation of transcription of a reporter molecule is measured after the cells are contacted by the test agent. In certain embodiments, the test agent is a chemical, small-molecule, biological molecule, polypeptide, polynucleotide, aptamer, or any combination thereof. In certain embodiments, a single test agent is applied to a population of cells. In certain embodiments, a plurality of test agents are applied to a population of cells.

In some embodiments, the method described herein measures GPCR activities by contacting a ligand with a GPCR expressed on the surface of the cell comprising the system described herein. In some embodiments, the method measures GPCR activities by contacting a plurality of ligands with a GPCR expressed on the surface of the cell comprising the system described herein. In some embodiments, the method measures GPCR activities by contacting a ligand with a plurality of GPCRs expressed on the surface of the cell comprising the system described herein. In some embodiments, the method measures GPCR activities by contacting a plurality of ligands with a plurality of GPCRs expressed on the surface of the cell comprising the system described herein.

In certain embodiments, the systems can be adapted for measuring responses of GPCR to test agents or ligands. The systems of the present disclosure can be adapted for use with any GPCR receptor. In certain embodiments, the systems are adapted for use with GPCR receptors by utilizing a cAMP response element regulated promoter. Non-limiting examples of GPCRs include 5-hydroxytryptamine receptors, acetylcholine receptors, adenosine receptors, adrenoceptors, angiotensin receptors, apelin receptor, bile acid receptor, bombesin receptors, bradykinin receptors, cannabinoid receptors, chemerin receptors, chemokine receptors, cholecystokinin receptors, dopamine receptors, endothelin receptors, formylpeptide receptors, free fatty acid receptors, galanin receptors, ghrelin receptor, glycoprotein hormone receptors, gonadotrophin-releasing hormone receptors, GPR18, GPR55, GPR119, G protein-coupled estrogen receptor, histamine receptors, hydroxycarboxylic acid receptors, kisspeptin receptors, leukotriene receptors, LPA receptors, S1P receptors, melanin-concentrating hormone receptors, melanocortin receptors, melatonin receptors, motilin receptor, neuromedin U receptors, neuropeptide FF/neuropeptide AF receptors, neuropeptide S receptor, neuropeptide W/neuropeptide B receptors, neuropeptide Y receptors, neurotensin receptors, opioid receptors, opsin receptors, orexin receptors, oxoglutarate receptor, P2Y receptors, platelet-activating factor receptor, prokineticin receptors, prolactin-releasing peptide receptor, prostanoid receptors, proteinase-activated receptors, QRFP receptor, relaxin family peptide receptors, somatostatin receptors, succinate receptors, tachykinin receptors, thyrotropin-releasing hormone receptors, trace amine receptors, urotensin receptor, vasopressin and oxytocin receptors, calcitonin receptors, corticotropin-releasing factor receptors, glucagon receptor family, parathyroid hormone receptors, VIP and PACAP receptors, calcium-sensing receptors, $GABA_B$ receptors, metabotropic glutamate receptors, taste 1 receptors, frizzled class receptors, adhesion class GPCRs, orphan receptors, or any combination thereof.

The nucleic acids of the present disclosure are compatible with many vectors common in the art. Non-limiting examples of vectors include genomic integrated vectors, episomal vectors, plasmids, viral vectors, cosmids, bacterial artificial chromosomes, and yeast artificial chromosomes. Non-limiting examples of viral vectors compatible with the nucleic acids of the present disclosure include vectors derived from lentiviruses, retroviruses, adenoviruses, and adeno-associated viruses. In certain embodiments, the nucleic acids of the present disclosure are present on vectors comprising sequences that direct site specific integration into a defined location or a restricted set of sites in the genome (e.g., AttP-AttB recombination).

In certain embodiments, the system described herein is incorporated into a single vector. In certain embodiments, the single vector is transfected into a cell transiently. In certain embodiments, the single vector is transfected into a cell stably.

In certain embodiments, the system is divided across two vectors. In certain embodiments, a first vector comprises a first regulatory element and a first effector, while a second vector comprises a second regulatory element for modulating the expression of a second effector. In certain embodiments, the first vector and the second vector are transiently transfected into a cell. In certain embodiments, the first vector and the second vector are stably transfected into a cell. In certain embodiments, the first vector is transfected into a cell stably and the second vector is transfected into a cell transiently. In certain embodiments, the first vector is transfected into a cell transiently and the second vector is transfected into a cell stably. In some embodiments, a separate vector comprising the reporter can be transfected into the cell. In some embodiments, the cell transfected with the first or second vector already comprises the reporter.

Vectors comprising the systems described herein or portions thereof may be constructed using many well-known molecular biology techniques. Detailed protocols for numerous such procedures, including amplification, cloning, mutagenesis, transformation, and the like, are described in, e.g., in Ausubel et al. Current Protocols in Molecular Biology (supplemented through 2012) John Wiley & Sons, New York 10 ("Ausubel"); Sambrook et al. Molecular Cloning—A Laboratory Manual (4th Ed.), Vol. 1-3, Cold Spring Harbor Laboratory, Cold Spring Harbor, New York, 2012 ("Sambrook"); and Abelson et al. Guide to Molecular Cloning Techniques (Methods in Enzymology) volume 152 Academic Press, Inc., San Diego, CA ("Abelson").

Kits

Disclosed herein, in some embodiments, are kits comprising the systems described herein. In some cases, the kit comprises at least one nucleic acid of the systems described herein. In some embodiments, the kit does not comprises a cell. In some embodiments, the kit comprises a cell transfected with the at least nucleic acid described herein. In some embodiments, the kit comprises a cell to be transfected with the at least nucleic acid described herein. In some embodiments, the kit disclosed herein can be used to measure GPCR activity in a cell. In some embodiments, the kit disclosed herein can be used to modulate GPCR activity in a cell. In some embodiments, the kit disclosed herein can be used to modulate G protein activity in a cell. In some embodiments, the kit disclosed herein can be used to modulate $G_i$ alpha subunit activity in a cell. In some embodiments, the kit disclosed herein can be used to modulate cAMP activity in a cell. In some embodiments, the kit disclosed herein can be used to modulate inverse cAMP activity in a cell. In some embodiments, the kit disclosed herein can be used to increase GPCR activity in a cell. In some embodiments, the kit disclosed herein can be used to increase G protein activity in a cell. In some embodiments, the kit disclosed herein can be used to increase $G_i$ alpha subunit activity in a cell. In some embodiments, the kit disclosed herein can be used to increase cAMP activity in a cell. In some embodiments, the kit disclosed herein can be used to increase inverse cAMP activity in a cell.

In some embodiments, the kit disclosed herein can be used to modulate expression of a GPCR effector in a cell. In some embodiments, the kit disclosed herein can be used to increase expression of a GPCR effector in a cell. In some embodiments, the kit disclosed herein can be used to decrease expression of a GPCR effector in a cell. In some embodiments, the kit disclosed herein can be used to increase expression of a first GPCR effector in a cell and decrease expression of a second GPCR effector in a cell. In some embodiments, the GPCR effector is an adenylyl cyclase. The adenylyl cyclase can be ADCY1, ADCY2, ADCY3, ADCY4, ADCY5, ADCY6, ADCY7, ADCY8, ADCY9, or ADCY10. In some embodiments, the kit disclosed herein can be used to increase expression of any one of the adenylyl cyclase. In some embodiments, the kit disclosed herein can be used to increase expression of ADCY6. In some embodiments, the kit disclosed herein can be used to decrease expression of any one of the adenylyl cyclase. In some embodiments, the kit disclosed herein can be used to decrease expression of ADCY3.

In some embodiments, the kit comprises the system described herein, which can be used to perform the methods described herein. Kits comprise an assemblage of materials or compositions, including at least one of the composition of the system. In other embodiments, the kits contains all of the compositions necessary and/or sufficient to perform the methods described herein, including all controls and directions.

In some instances, the kits described herein comprise the systems described herein for modulating the gene activity of any one of the transgenes described herein. The exact nature of the components configured in the kit depends on its intended purpose. For example, some kits can be configured for screening GPCR activities of a ligand binding or complexing to a GPCR. In some embodiments, the kit can be configured particularly for the purpose screening for an unknown ligand. In some embodiments, the kit can be configured particularly for measuring GPCR activities stimulated by a ligand or in the absence of an ligand.

In some cases, instructions for use can be included in the kit. Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of the pharmaceutical composition. The packaging material has an external label which indicates the contents and/or purpose of the kit and its components.

While preferred embodiments of the systems and methods have been shown and described herein, it will be obvious to those skilled in the art that such embodiments are provided by way of example only. It is not intended that the systems and methods be limited by the specific examples provided within the specification. While the systems and methods have been described with reference to the aforementioned specification, the descriptions and illustrations of the embodiments herein are not meant to be construed in a limiting sense. Numerous variations, changes, and substitutions will now occur to those skilled in the art without departing from the present disclosure. Furthermore, it shall be understood that all aspects of the systems and methods are not limited to the specific depictions, configurations or relative proportions set forth herein which depend upon a variety of conditions and variables. It should be understood that various alternatives to the embodiments of the systems and methods described herein may be employed in practicing the present disclosure. It is therefore contemplated that the systems and methods described herein shall also cover any such alternatives, modifications, variations or equivalents. It is intended that the following claims define the scope of the systems and methods described herein and that the systems and methods described herein are within the scope of these claims and their equivalents be covered thereby.

Embodiments

Embodiment 1. A system for measuring G protein-coupled receptor (GPCR) activity, the system comprising: a first effector of the GPCR activity, wherein an expression of the first effector is upregulated compared to an expression of the first effector in a wild-type state; and a second effector of the GPCR activity, wherein an expression of the second effector is downregulated compared to an expression of the second effector in a wild-type state.

Embodiment 2. The system of Embodiment 1, wherein the expression of the first effector is upregulated by contacting a GPCR with a GPCR activator.

Embodiment 3. The system of Embodiment 2, wherein the GPCR activator is a GPCR agonist.

Embodiment 4. The system of Embodiment 2 wherein the GPCR activator is an agonist of the first effector.

Embodiment 5. The system of Embodiment 1, wherein the system comprises a first nucleic acid encoding the first effector of the GPCR activity is operably coupled to a regulatory element for upregulating expression of the first effector.

Embodiment 6. The system of Embodiment 1, wherein the expression of the second effector is downregulated by contacting a GPCR with a GPCR inhibitor.

Embodiment 7. The system of Embodiment 6, wherein the GPCR inhibitor is a GPCR inverse agonist.

Embodiment 8. The system of Embodiment 6, wherein the GPCR inhibitor is a GPCR antagonist.

Embodiment 9. The system of Embodiment 6, wherein the GPCR inhibitor is an inverse agonist of the second effector.

Embodiment 10. The system of Embodiment 6, wherein the GPCR inhibitor is an antagonist of the second effector.

Embodiment 11. The system of Embodiment 1, wherein the system comprises a second nucleic acid that downregulates the expression of the second effector.

Embodiment 12. The system of Embodiment 1, wherein the GPCR activity comprises a Gi alpha subunit activity, a Gs alpha subunit activity, a Gq alpha subunit activity, or a G12/13 alpha subunit activity.

Embodiment 13. The system of Embodiment 12, wherein the GPCR activity comprises the Gi alpha subunit activity.

Embodiment 14. The system of Embodiment 13, wherein the Gi alpha subunit activity comprises activity of $G\alpha i1$, $G\alpha i2$, $G\alpha i3$, $G\alpha o$, $G\alpha t$, $G\alpha g$ or $G\alpha z$.

Embodiment 15. The system of Embodiment 12, wherein the GPCR activity comprises the Gs alpha subunit activity.

Embodiment 16. The system of Embodiment 12, wherein the GPCR activity comprises the Gq alpha subunit activity.

Embodiment 17. The system of Embodiment 12, wherein the GPCR activity comprises the $G_{12/13}$ alpha subunit activity.

Embodiment 18. The system of Embodiment 5, wherein the regulatory element is inducible.

Embodiment 19. The system of Embodiment 5, wherein the regulatory element is constitutively active.

Embodiment 20. The system of any one previous Embodiments, wherein the first effector comprises a first adenylyl cyclase.

Embodiment 21. The system of Embodiment 20, wherein the first adenylyl cyclase is selected from the group consisting of ADCY1, ADCY2, ADCY3, ADCY4, ADCY5, ADCY6, ADCY7, ADCY8, ADCY9, and ADCY10.

Embodiment 22. The system of Embodiment 21, wherein the first adenylyl cyclase is ADCY6.

Embodiment 23. The system of any one of previous Embodiments, wherein the second effector comprises a second adenylyl cyclase.

Embodiment 24. The system of Embodiment 23, wherein the second adenylyl cyclase is selected from the group consisting of ADCY1, ADCY2, ADCY3, ADCY4, ADCY5, ADCY6, ADCY7, ADCY8, ADCY9, and ADCY10.

Embodiment 25. The system of Embodiment 24, wherein the second adenylyl cyclase is ADCY3.

Embodiment 26. The system of any one of Embodiments 12-25, wherein the second nucleic acid comprises a microRNA, a shRNA, a siRNA, a gRNA, or a combination thereof.

Embodiment 27. The system of Embodiment 26, wherein the second nucleic acid comprises the microRNA.

Embodiment 28. The system of Embodiment 26, wherein the second nucleic acid comprises the gRNA.

Embodiment 29. The system of Embodiment 28. further comprises a CRISPR-Cas system operatively coupled to the gRNA.

Embodiment 30. The system of Embodiment 1, wherein the GPCR activity comprises cyclic AMP (cAMP) activity.

Embodiment 31. The system of Embodiment 1, wherein the GPCR activity comprises a change in cAMP concentration.

Embodiment 32. The system of Embodiment 1, wherein the GPCR activity comprises an inverse cAMP activity.

Embodiment 33. The system of Embodiment 20, wherein the system increases the cAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a cAMP activity in a cell without the system.

Embodiment 34. The system of Embodiment 31 wherein the system increases the cAMP concentration in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a cAMP concentration in a cell without the system.

Embodiment 35. The system of Embodiment 32, wherein the system increases the inverse cAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to an inverse cAMP activity in a cell without the system.

Embodiment 36. The system of any one of previous Embodiments, wherein the system comprises a second regulatory element for upregulating expression of a Gi alpha subunit.

Embodiment 37. The system of any one of previous Embodiments, wherein the system comprises at least one additional effector.

Embodiment 38. The system of Embodiment 37, wherein the at least one additional effector is an adenylyl cyclase.

Embodiment 39. The system of Embodiment 37, wherein the system further comprises a second regulatory element for upregulating expression of the at least one additional effector.

Embodiment 40. The system of any one of previous Embodiments, wherein the system increases a ratio between the GPCR activity and a background in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a ratio between the GPCR activity and the background in a cell without the system.

Embodiment 41. The system of Embodiment 40, wherein the system increases the GPCR activity in the cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the GPCR activity in the cell without the system.

Embodiment 42. The system of Embodiment 40, wherein the system decreases the background in the cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the background in the cell without the system.

Embodiment 43. The system of any one of previous Embodiments, wherein the system comprises a reporter nucleic acid, wherein the reporter nucleic acid generates a detectable signal that is proportional to the GPCR activity.

Embodiment 44. The system of Embodiment 43, wherein the reporter nucleic acid comprises a cAMP response element (CRE) sequence.

Embodiment 45. The system of Embodiment 43, wherein the reporter nucleic acid is operatively coupled to an unique molecular identifier (UMI) nucleic acid sequence.

Embodiment 46. The system of Embodiment 43, wherein the detectable signal comprises a fluorescent signal.

Embodiment 47. The system of Embodiment 43, wherein the detectable signal comprises a luminescent signal.

Embodiment 48. The system of Embodiment 5, wherein the first nucleic acid comprises a gene expression cassette for upregulating the expression of the first effector.

Embodiment 49. The system of Embodiment 11, wherein the second nucleic acid comprises a gene expression cassette for downregulating the expression of the second effector.

Embodiment 50. A cell comprises the system of any one of Embodiments 1-49.

Embodiment 51. The cell of Embodiment 50, wherein the cell comprises an eukaryotic cell.

Embodiment 52. The cell of Embodiment 50, wherein the cell comprises a mammalian cell.

Embodiment 53. The cell of Embodiment 50, wherein the comprises a mammalian cell-derived cell.

Embodiment 54. The cell of Embodiment 50, wherein the cell is derived from a cell line.

Embodiment 55. The cell of Embodiment 50, wherein the cell is selected from the group consisting of a CHO-K1 cell, a COS-7 cell, and an U2OS cell.

Embodiment 56. The cell of any one of Embodiments 50-55, wherein the system is integrated into a genome of the cell.

Embodiment 57. A cell population comprising the cell of any one of Embodiments 52-57.

Embodiment 58. The cell population of Embodiment 57, wherein the cell population comprises a population of eukaryotic cells.

Embodiment 59. The cell population of Embodiment 57, wherein the cell population comprises a population of mammalian cells.

Embodiment 60. The cell population of Embodiment 57, wherein the cell population comprises a population mammalian cell-derived cells.

Embodiment 61. The cell population of Embodiment 55, wherein the cell population comprises a population of cells derived from a cell line.

Embodiment 62. The cell population of Embodiment 55, wherein the cell population comprises a population of cells selected from the group consisting of CHO-K1 cells, COS-7 cells, and U2OS cells.

Embodiment 63. A method for measuring the GPCR activity comprises measuring the GPCR activity in the cell of any one of Embodiments 50-56 or the cell population of any one of Embodiments 57-62.

Embodiment 64. The method of Embodiment 63, wherein the GPCR activity is basal GPCR activity.

Embodiment 65. The method of Embodiment 63, wherein the cell of any one of Embodiments 50-56 or the cell population of any one of Embodiments 57-62 is not contacted with a GPCR ligand.

Embodiment 66. A method for measuring the GPCR activity in a cell, the method comprising contacting the cell of any one of Embodiments 50-56 or the cell population of any one of Embodiments 57-62 with a GPCR ligand, wherein the ligand complexes with the GPCR and initiates or inhibits the GPCR activity.

Embodiment 67. The method of Embodiment 66, wherein the GPCR ligand is expressed in the cell of any one of Embodiments 50-56.

Embodiment 68. The method of Embodiment 67, wherein the GPCR ligand is selected from the group consisting of a polypeptide, a non-peptide compound, and a small molecule.

EXAMPLES

The following illustrative examples are representative of embodiments of the stimulation, systems, and methods described herein and are not meant to be limiting in any way.

Example 1. GPCR Activity Measurements

GPCR activity was measured from cells transfected with different plasmids as shown in FIGS. 2A-2C. The plasmid described in FIG. 2A contained a gene expression cassette that coded for a miRNA array that targeted the endogenous adenylyl cyclase 3 (AC3) mRNA for downregulation. This cassette also contained an exogenous sequence that coded for the production of the adenylyl cyclase 6 (AC6) protein. Both of these elements were under control of the same cumate controlled promoter. This nucleic acid also contained a second cassette that codes for the production of a gene that provided resistance to the antibiotic blasticidin. The plasmid was stably integrated into a HEK 293 cell line by co-transfecting with a second plasmid containing an expression cassette with the bxbi integrase. The cell line and the plasmid contained the bxbi integration sequences, allowing for integration of the plasmid at a specific locus in the genome at single copy. The cell line also contained expression cassettes coding for the production of the cumate repressor protein, which allowed for cumate inducible expression of cumate controlled promoters, and the reverse-tetracycline-transactivator (rTTA) protein that allowed for doxycycline inducible expression. Successful integration was selected for by passaging the cells in blasticidin supplemented media.

The plasmid described in FIG. 2B contained a gene expression cassette that coded for a dCas9-BFP-KRAB fusion protein and multiple expression cassettes that coded for 3 different RNA guides (gRNA) that targeted AC3. Downregulation was achieved through targeting of the dCas9-BFP-KRAB to the native AC3 genomic locus by the gRNAs. The plasmid also contained a gene expression cassette coding for hygromycin resistance and sleeping beauty transposon integration sequences. Two different plasmids, each containing 3 guides to AC3 (for a total of 5 unique guides), were stably integrated into the bxbi integrated cell line described above, by co-transfection with a plasmid coding for the expression of the sleeping beauty transposase. Successful integration was selected for by pas-
saging the cells in hygromycin supplemented media.

The plasmid described in FIG. 2C contained a gene
expression cassette under a cumate controlled promoter that
coded for the production of AC6 protein. This plasmid also 5
contained a second gene expression cassette that coded for
the production of the cumate repressor protein, that allowed
for cumate inducible expression of cumate controlled pro-
moters, and the puromycin resistance gene. This plasmid
also contained piggybac transposon integration sequences. 10
The plasmid was stably integrated into the HEK 293 cell line
described above by co-transfecting with a plasmid coding
for the expression of the piggybac transposase. Successful
integration was selected for by passaging the cells in puro-
mycin supplemented media. Nucleic acid sequences of the 15
plasmids of FIGS. 2A-2C can be found in SEQ ID NOs: 1-4.

Figure 3:
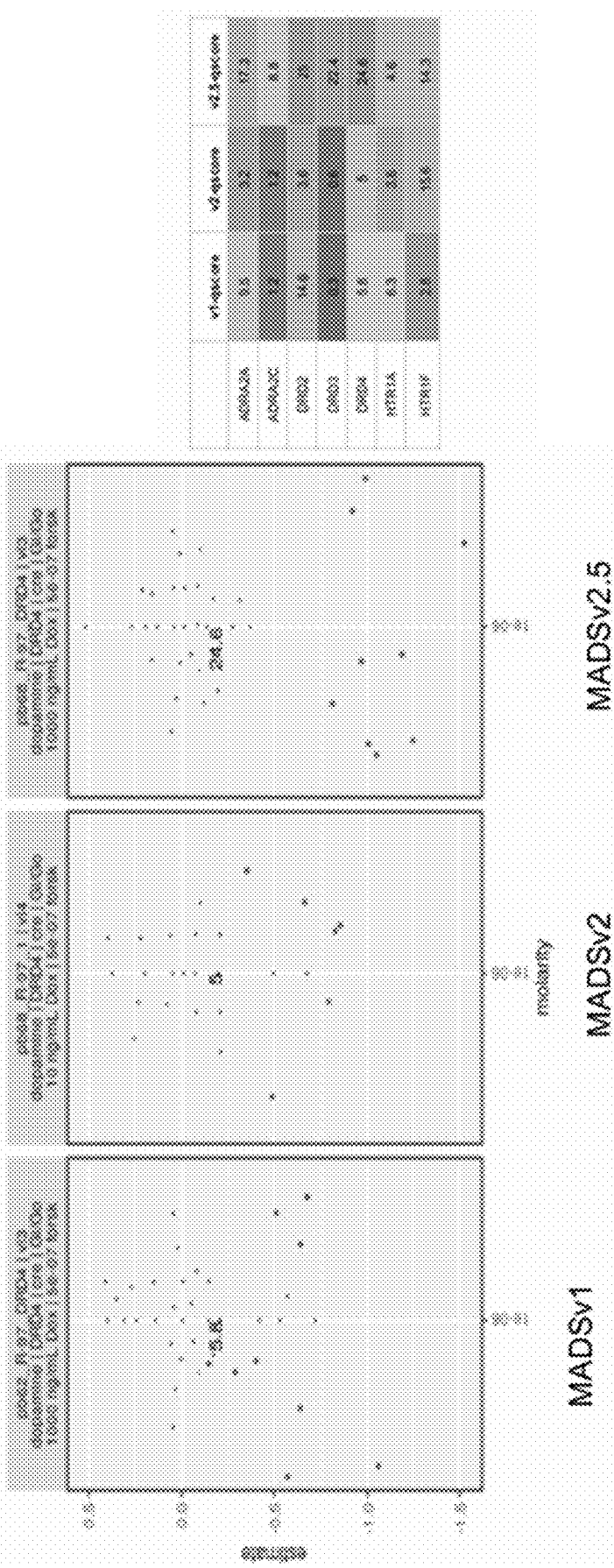
FIG. 3 illustrates increased GPCR activity by altering AC expression (MADSv2.5 cassette, e.g. second-generation gene expression cassette of FIG. 2A).
Figure 4:
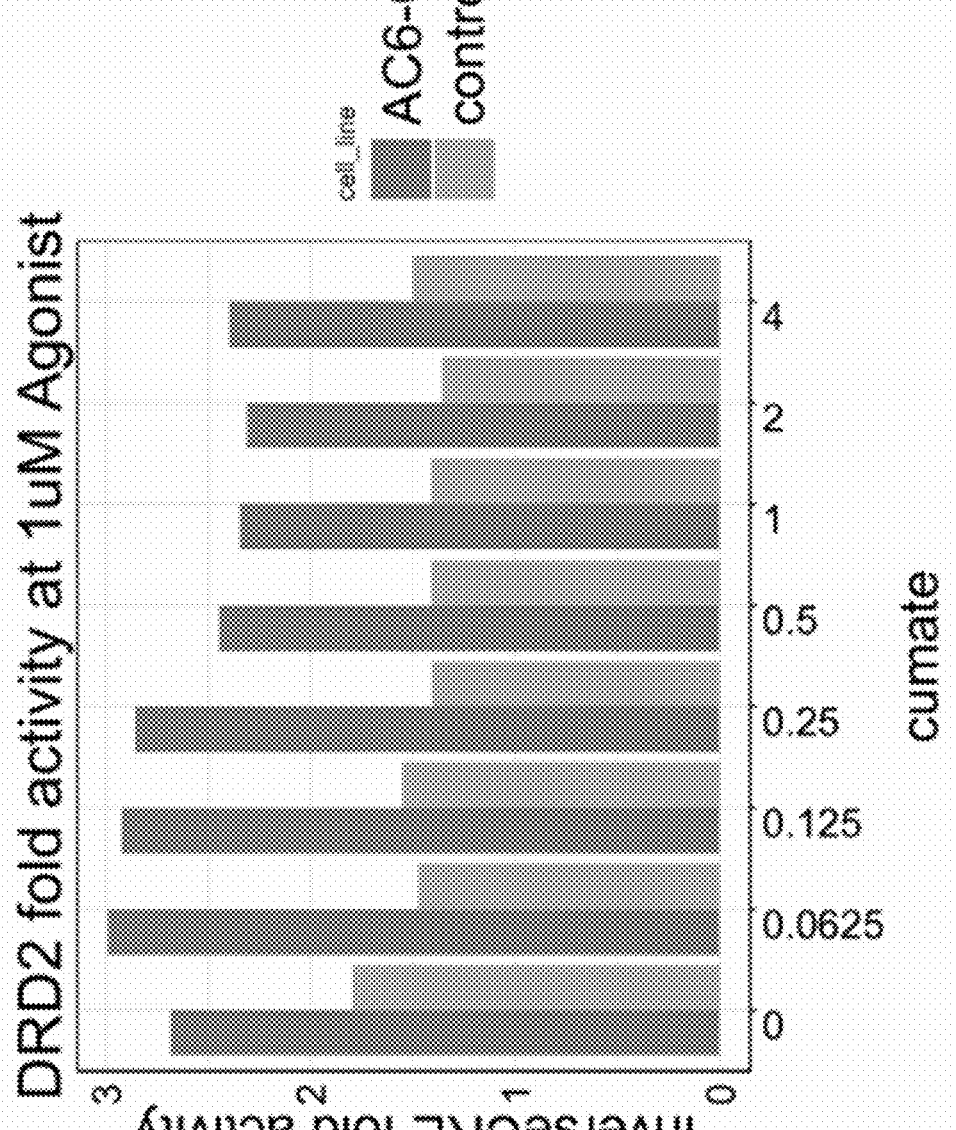
FIG. 4 illustrates luciferase measurements generated from cells comprising the first-generation gene expression cassette of FIG. 2C, showing increased inverse CRE activity with just AC6 overexpression.
Figure 5:
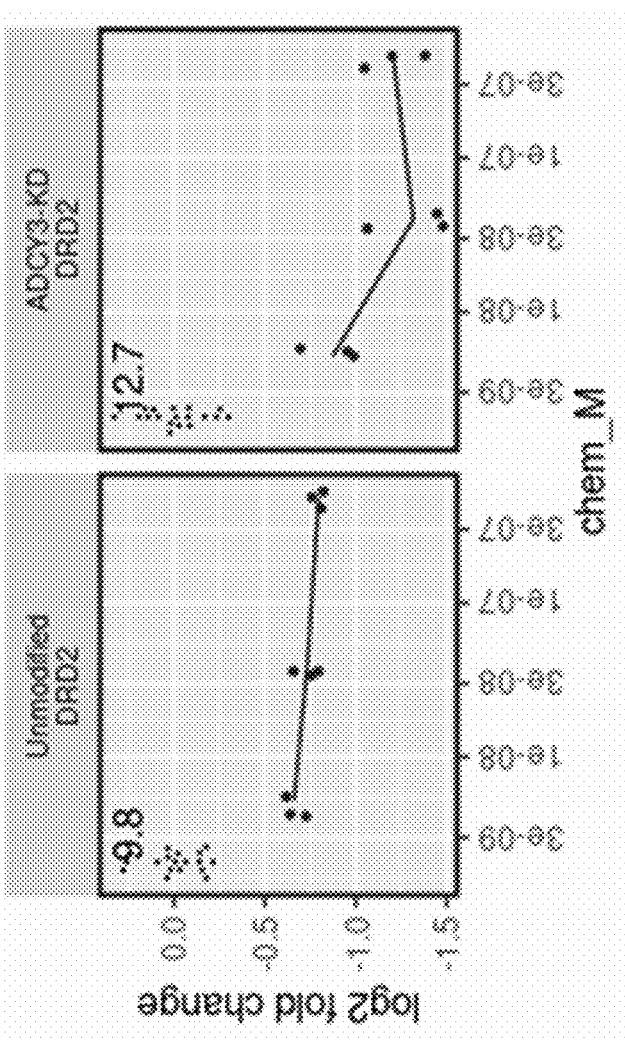
FIG. 5 illustrates platform data generated from cells comprising the third-generation gene expression cassette of FIG. 2B (comprising AC3 knockdown), showing improvement over the platform data generated from cells comprising the second-generation gene expression cassette described herein.

The cells transfected with the second-generation gene
expression cassette (FIG. 2A) were contacted with dop-
amine and 0.5 µM forskolin (Fsk) (FIG. 3). As shown in
FIG. 3, the GPCR activities associated with adrenaline, 20
adrenaline, dopamine, dopamine, dopamine, and serotonin
binding to receptors of ADRA2A, ADRA2C, DRD2, DRD3,
DRD4, and HTR1F respectively were increased in the cells
transfected with the MADSv2.5 nucleic acid. As shown in
FIG. 4, the luciferase measurements generated by cells comprising the first-generation gene expression cassette
(FIG. 2C), showing increased inverse CRE activity with just
AC6 overexpression (AC6-OE). As seen in FIG. 5, the
platform data generated from cells comprising the third-
generation cassette (FIG. 2B, comprising AC3 knockdown,
ADCY3-KD), showing improvement over the platform data
generated from cells comprising the second-generation gene
expression cassette, where ADCY3 knockdown led to
decreased measured activity.

While the foregoing disclosure has been described in
some detail for purposes of clarity and understanding, it will
be clear to one skilled in the art from a reading of this
disclosure that various changes in form and detail can be
made without departing from the true scope of the disclo-
sure. For example, all the techniques and apparatus
described above can be used in various combinations. All
publications, patents, patent applications, and/or other docu-
ments cited in this application are incorporated by reference
in their entirety for all purposes to the same extent as if each
individual publication, patent, patent application, and/or
other document were individually and separately indicated
to be incorporated by reference for all purposes. Definitions
that are contained in text incorporated by reference are
excluded to the extent that they contradict definitions in this
disclosure.

The invention claimed is:

1. A system for measuring G protein-coupled receptor (GPCR) activity in a mammalian cell, the system comprising:

a) a first exogenous effector of GPCR activity, wherein an expression of the first exogenous effector of GPCR activity is upregulated compared to an expression of the first exogenous effector of GPCR activity in a wild-type state, wherein the first exogenous effector of GPCR activity comprises a first adenylyl cyclase comprising ADCY6;

b) a second exogenous effector of GPCR activity, wherein an expression of the second exogenous effector of GPCR activity is downregulated compared to an expression of the second exogenous effector of GPCR activity in a wild-type state, wherein the second exogenous effector of GPCR activity comprises a second adenylyl cyclase comprising ADCY3; and c) a reporter nucleic acid, wherein the reporter nucleic acid comprises a unique molecular identifier (UMI) nucleic acid sequence.

2. The system of claim 1, wherein the GPCR activity comprises a $G_i$ alpha subunit activity, a $G_8$ alpha subunit activity, a $G_q$ alpha subunit activity, or a $G_{12/13}$ alpha subunit activity.

3. The system of claim 2, wherein the $G_i$ alpha subunit activity comprises activity of Gαi1, Gαi2, Gαi3, Gαo, Gαt, Gαg, or Gαz.

4. The system of claim 2, wherein the GPCR activity comprises the $G_s$ alpha subunit activity, the $G_q$ alpha subunit activity, or the $G_{12/13}$ alpha subunit activity.

5. The system of claim 1, wherein the system increases a ratio between the GPCR activity and a background in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a ratio between the GPCR activity and the background in a cell without the system.

6. The system of claim 1, wherein the system increases the GPCR activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the GPCR activity in the cell without the system.

7. The system of claim 1, wherein the system decreases the background in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to the background in the cell without the system.

8. The system of claim 5, wherein the first adenylyl cyclase is encoded by a nucleic acid operatively coupled to a promoter or enhancer that overexpresses the first adenylyl cyclase compared to a wild-type state.

9. The system of claim 1, wherein the GPCR activity comprises inverse cAMP activity.

10. The system of claim 9, wherein the system increases the inverse cAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to an inverse CAMP activity in a cell without the system.

11. The system of claim 9, wherein the system increases the CAMP activity in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a CAMP activity in a cell without the system.

12. The system of claim 1, wherein the second adenylyl cyclase is targeted by one or more of a microRNA, an shRNA, an siRNA, or a CRISPR/Cas9 complex that reduces expression of the second adenylyl cyclase compared to a wild-type state.

13. The system of claim 1, wherein the reporter nucleic acid generates a detectable signal from a reporter gene that is proportional to the GPCR activity.

14. The system of claim 1, wherein the reporter nucleic acid comprises a cAMP response element (CRE) sequence operatively coupled to the reporter gene.

15. The system of claim 1, wherein the GPCR activity comprises a CAMP concentration in a cell, wherein the system increases the cAMP concentration in a cell comprising the system by at least 1 fold, 2 fold, 3 fold, 4 fold, 5 fold, 6 fold, 7 fold, 8 fold, 9 fold, 10 fold, 20 fold, 50 fold, or 100 fold compared to a CAMP concentration in a cell without the system.

16. The system of claim 14, wherein the reporter gene comprises one or more of: a fluorescent signal, or a luminescent signal.

17. The system of claim 1, wherein the mammalian cell is selected from the group consisting of a HEK 293 cell, a CHO-K1 cell, a COS-7 cell, and an U2OS cell.

18. The system of claim 1, wherein the system is integrated into a genome of the mammalian cell.

* * * * *